United States Patent [19]
Zeng et al.

[11] Patent Number: 6,069,689
[45] Date of Patent: May 30, 2000

[54] APPARATUS AND METHODS RELATING TO OPTICAL SYSTEMS FOR DIAGNOSIS OF SKIN DISEASES

[75] Inventors: Haishan Zeng, Delta; Harvey Lui, Vancouver; Calum MacAulay, Vancouver; Branko Palcic, Vancouver; David I. McLean, Vancouver, all of Canada

[73] Assignee: Derma Technologies, Inc., Canada

[21] Appl. No.: 09/059,885

[22] Filed: Apr. 14, 1998

Related U.S. Application Data

[63] Continuation-in-part of application No. 08/843,605, Apr. 16, 1997, Pat. No. 6,008,889.

[51] Int. Cl.[7] .............................. G01B 9/02; G01N 11/00
[52] U.S. Cl. ......................... 356/73; 356/318; 356/326; 356/445
[58] Field of Search .............................. 356/73, 318, 326, 356/445–448; 128/633, 664, 665; 385/901, 116; 600/473–476

[56] References Cited

U.S. PATENT DOCUMENTS

| | | | |
|---|---|---|---|
| 4,718,417 | 1/1988 | Kittrell et al. | 606/7 |
| 4,768,513 | 9/1988 | Suzuki | 600/476 |
| 4,847,198 | 7/1989 | Nelson et al. | 435/34 |
| 4,927,222 | 5/1990 | Kamiya et al. | 385/50 |
| 4,930,516 | 6/1990 | Alfano et al. | 600/477 |
| 4,957,114 | 9/1990 | Zeng et al. | 600/476 |
| 5,042,494 | 8/1991 | Alfano | 600/477 |
| 5,131,398 | 7/1992 | Alfano et al. | 600/476 |
| 5,261,410 | 11/1993 | Alfano | 600/475 |
| 5,280,788 | 1/1994 | Janes et al. | 600/476 |
| 5,348,018 | 9/1994 | Alfano et al. | 600/476 |
| 5,413,108 | 5/1995 | Alfano | 600/476 |
| 5,439,000 | 8/1995 | Gunderson et al. | 600/473 |
| 5,452,723 | 9/1995 | Wu et al. | 600/342 |
| 5,456,260 | 10/1995 | Kollias et al. | 600/477 |

(List continued on next page.)

OTHER PUBLICATIONS

Andrew J. Berger, et al., Rapid, noninvasive concentration measurements of aqueous biological analytes by near–infrared Raman spectroscopy, Applied Optics, Jan. 1, 1996, vol. 35, No. 1, pp. 209–212.

Zeng, et al., "Optical spectroscopy studies of diseased skin," European BioMedical Optics–BiOS Europe '95, Barcelona, Spain, Sep. 12–16, 1995 (p. 145).

Zeng, et al., "Non–invasive, Bedside Autofluorescence Spectroscopy of Benign and Malignant Skin Lesions," Fourth Meeting of the Western Canadian Society for Clinical and Investigative Dermatology, Jasper, AB, Mar. 24–26, 1995.

Zeng, et al., "Quantative Analysis of Laser Induced Autofluorescence Spectra of Diseased Skin," Photonics China '96, Lasers in Medicine and Dentistry: Dignostics and Treatment, Bejing, China, Nov. 4–7, 1996.

(List continued on next page.)

*Primary Examiner*—Robert H. Kim
*Assistant Examiner*—Michael P. Stafira
*Attorney, Agent, or Firm*—Fulwilder Patton Lee & Utecht, LLP

[57] ABSTRACT

Apparatus for diagnosis of a skin disease site using spectral analysis includes a light source for generating light to illuminate the disease site and a probe unit optically connected to the light source for exposing the disease site to light to generate fluorescence and reflectance light. The probe unit also collects the generated fluorescence and reflectance light and transmits this light to a spectrometer to be analyzed. The spectrometer generates and displays spectral measurements of the fluorescence light and the reflectance light which in together assist the user in diagnosing the disease site. The apparatus makes use of a conventional personal computer using a plug-in spectrometer card to provide a compact and low costs system. The system performs combined fluorescence and reflectance spectral analysis in a quick and efficient manner to provide a powerful tool for dermatologic diagnosis.

21 Claims, 17 Drawing Sheets

U.S. PATENT DOCUMENTS

| | | | |
|---|---|---|---|
| 5,467,767 | 11/1995 | Alfano et al. | 600/476 |
| 5,507,287 | 4/1996 | Palcic et al. | 600/317 |
| 5,522,868 | 6/1996 | Buckley et al. | 607/94 |
| 5,556,612 | 9/1996 | Anderson et al. | 424/59 |
| 5,590,660 | 1/1997 | MacAulay et al. | 600/478 |
| 5,601,087 | 2/1997 | Gunderson et al. | 600/473 |
| 5,615,673 | 4/1997 | Berger et al. | 128/633 |
| 5,647,368 | 7/1997 | Zeng et al. | 600/476 |
| 5,687,730 | 11/1997 | Doiron et al. | 600/447 |
| 5,693,043 | 12/1997 | Kittrell et al. | 606/15 |
| 5,697,373 | 12/1997 | Richards-Kortum et al. | 600/475 |
| 5,699,795 | 12/1997 | Richards-Kortum et al. | 600/478 |
| 5,701,902 | 12/1997 | Vari et al. | 600/473 |
| 5,705,518 | 1/1998 | Richter et al. | 514/410 |
| 5,738,101 | 4/1998 | Sappey | 600/476 |
| 5,751,415 | 5/1998 | Smith et al. | 356/301 |
| 5,753,511 | 5/1998 | Selinfreund | 436/20 |
| 5,769,081 | 6/1998 | Alfano et al. | 128/665 |
| 5,778,016 | 7/1998 | Sucha et al. | 372/38 |
| 5,784,162 | 7/1998 | Cabib et al. | 356/346 |
| 5,786,893 | 7/1998 | Fink et al. | 356/301 |

OTHER PUBLICATIONS

Zeng, et al., "Update on Fluorescence Spectroscopy Studies of Diseased Skin," SPIE BiOS '96, San Jose, CA, Jan. 27–Feb. 2, 1996, Paper 2671E–42, Session 8, p. 12.

Lui, et al., "Ratio Analysis of Reflectance and Fluorescence Spectra of Diseased Skin," 24$^{th}$ Annual Meeting of the American Society for Photobiology, Atlanta, Georgia, Jun. 15–20, 1996.

Lui, et al., "Optical Spectroscopy as a Potential Diagnostic Aid for Dermatology," Clinical Dermatology 2000—International Congress, Vancouver, BC, May 28–31, 1996, Programme and Abstracts, Abstract 584, p. 176.

Richter, et al., "Photosensitising potency of structural analogues of benzoporphyrin derivative (BPD) in a mouse tumour model," Cancer (1991) 63, 87–93.

Zeng, et al., "Miniature Spectrometer and Multi–Spectral Imager for Skin Diagnoses," Laser in Dermatology, Plastic Surgery and Burn Treatment at Biomedical Optics '95, San Jose, CA, Feb. 4–10, 1995, In: SPiE 238709:17, 1995.

Zeng et al., "Update on fluorescence spectroscopy studies of diseased skin," Conference: Lasers in Dermatology and Plastic Surgery, BiOS '96, Jan. 27–Feb. 2, 1996, San Jose, CA.

Zeng et al., "Optical spectroscopy studies of diseased skin—preliminary results," SPIE vol. 2628 / 281–285 (1995).

Zeng et al., "Miniature spectrometer and multi–spectral imager as a potential diagnostic aid in dermatology," SPIE vol. 2387 / 57–61 (1995).

Richter et al., "Preliminary Studies on a More Effective Phototoxic Agent Than Hematophorphyrin," JNCI. vol. 79. No. 6, Dec., 1987, pp. 1327–1332.

Zeng, et al., "Novel Microspectrophotometer and its Biomedical Applications", Optical Engineering, SPIE vol. 32: No. 8, 1809–1814 (1993).

Zeng, et al., "Laser–induced changes in autofluorescence of in vivo skin", Laser–Tissue Interaction IV, SPIE vol. 1882:278–290 (1993).

Bissonnette R.et al., "Detection of Autofluorescence Due to Protoporphyrin IX in the Stratum Corneum of Ps oriasis Plaques," 25$^{th}$ Annual Meeting of the American Society for Photobiology, St. Louis, Missouri, Jul. 5–10, 1997.

Zeng, et al., "Reconstruction of in vivo skin autofluorescence spectrum from microscopic properties by Monte Carlo simulation", Journal of Photochemistry and Photobiology B: Biology, 234–240 (1996).

Zeng, et al., "Spectroscopic and Microscopic Characteristics of Human Skin Autofluorescence Emission", Photochemistry and Photobiology, 61:639–645, 1995.

Tanaka K. et al., "Compound parabolic concentrator probe for efficient light collection in spectroscopy of biological tissue", Applied Optics, 35(4):758–763 (1996).

Williams AC et al., "A Critical Comparison of Some Raman Spectroscopic Techniques for Studies of Human Stratum Corneum", Pharmaceutical Research, 10 (11): 1642–1647 (1993).

Williams AC et al., "Comparison of Fourier Transform Raman Spectra of Mammalian and Reptilian Skin", Analyst, vol. 119:563–566 (1994).

Zeng H et al., "A computerized autofluorescence and diffuse reflectance spectroanalyser system for in vivo skin studies", Phys. Med. Biol. vol. 38:231–240 (1993).

Zeng H et al., "Monte Carlo modeling of tissue autofluorescence measurement and imaging", from Proceedings of Advances in Laser and Light Spectroscopy to Diagnose Cancer and Other Diseases; SPIE vol. 2135:94–104 (1994).

Barry BW, et al., "Fourier Transform Raman and Infrared Vibrational Study of Human Skin: Assignment of Spectral Bands", Journal of Raman Spectroscopy, 23:641–645 (1992).

Mahadevan–Jansen A. et al., "Raman Spectroscopy for the Detection of Cancers and Precancers," Journal of Biomedical Optics 1(1), 31–70 (Jan. 1996).

Manoharan R.et al., Histochemical analysis of biological tissues using Raman spectroscopy, Spectrochimica Acta Part A 52:215–249 (1996).

Mizuno A.et al., "Near–Infrared Fourier Transform Raman Spectroscopic Study of Human Brain Tissues and Tumours", Journal of Raman Spectroscopy, 25:25–29 (1994).

Ono I. et al., "Magnetic Resonance Imaging for Diagnosing Skin Tumors", Clinics in Dermatology, 13:393–399 (1995).

Redd D. CB et al., Raman Spectroscopic Charaterization of Human Breast Tissues: Implications for Breast Cancer Diagnosis, Applied Spectroscopy, 47:6: 787–791 (1993).

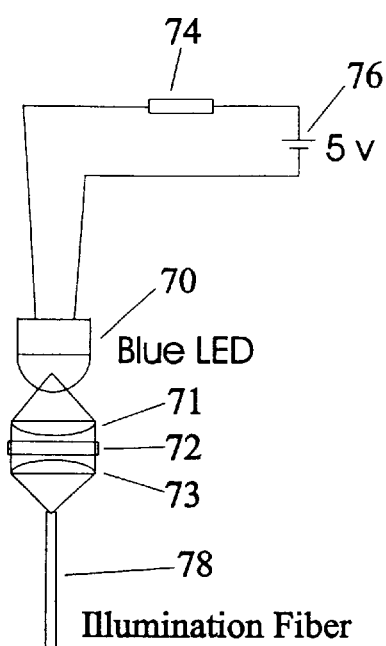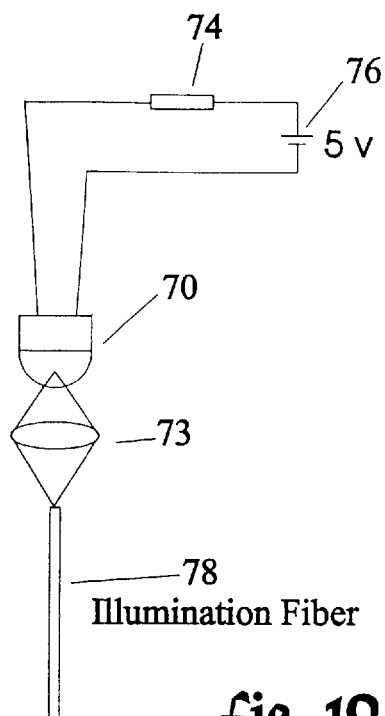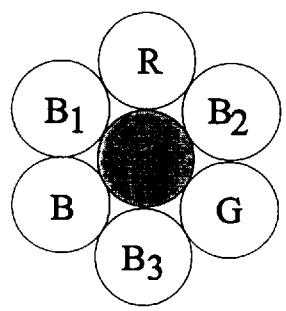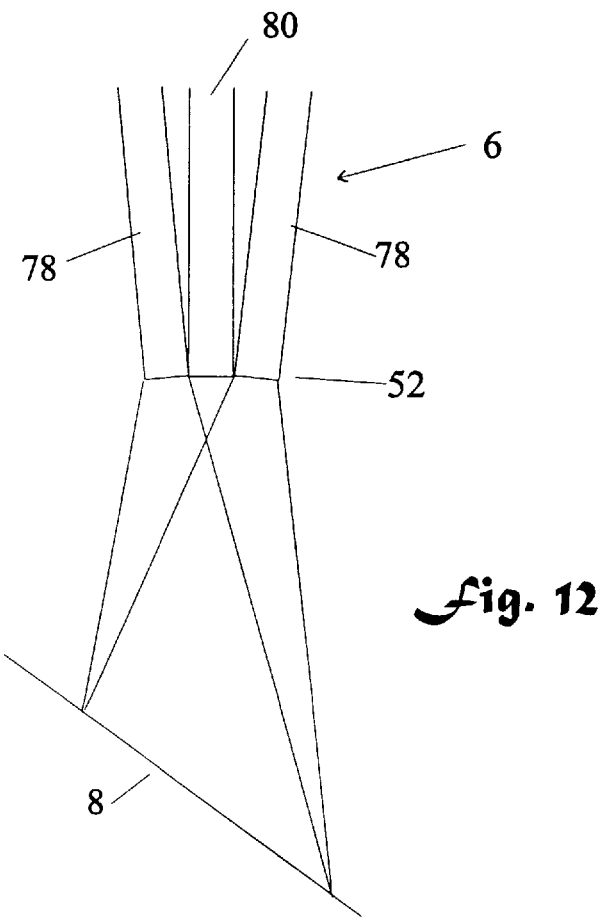

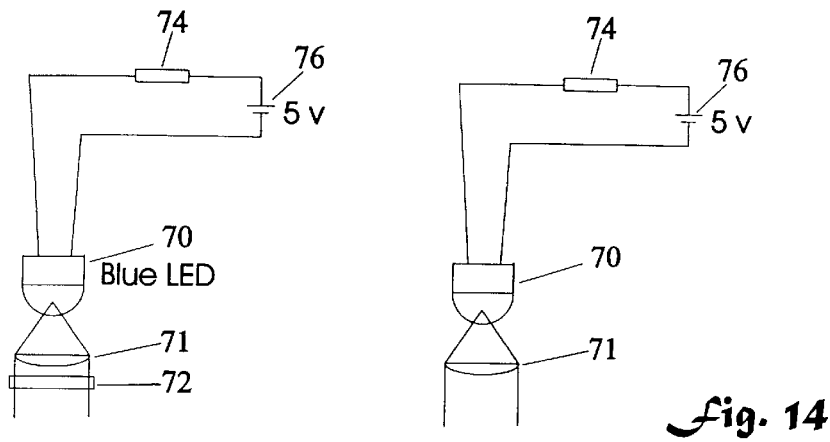
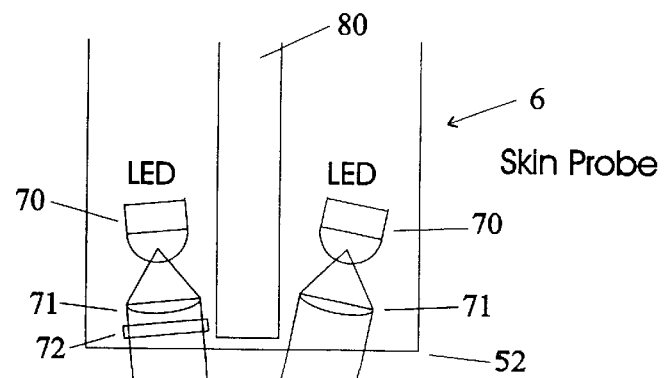
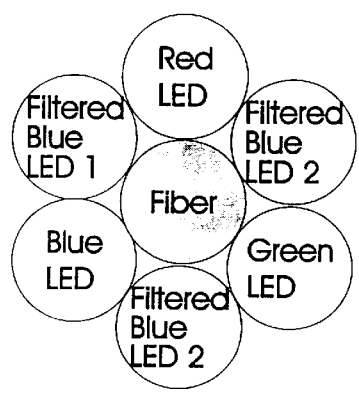
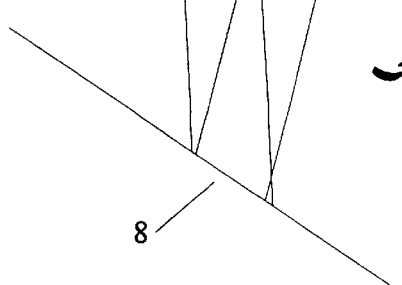
Fig. 13
Fig. 14
Fig. 15
Fig. 16

APPARATUS AND METHODS RELATING TO OPTICAL SYSTEMS FOR DIAGNOSIS OF SKIN DISEASES

CROSS-REFERENCE TO RELATED APPLICATION

This application is a continuation-in-part of U.S. patent application No. 08/843,605, filed Apr. 16, 1997, now U.S. Pat. No. 6,008,889.

TECHNICAL FIELD OF THE INVENTION

This invention relates to apparatus and methods for assisting in diagnosis of skin diseases by making measurements of fluorescence light and/or reflectance light and/or Raman scattering from the skin disease sites.

BACKGROUND OF THE INVENTION

Currently, clinical diagnosis of skin disease is generally accomplished by visual inspection under white light illumination. In this process, the reflectance light of a skin lesion is examined. Visual diagnosis alone may not be particularly accurate for early detection of skin cancer since many skin conditions have a similar appearance under white light. Therefore, when a suspect lesion is identified by visual examination, a biopsy is often performed for a definitive diagnosis. This is because it is crucial to diagnose skin pre-cancer or cancer at an early stage when it is curable. Thus, it is important to improve the clinical diagnosis of suspected skin lesions so as to avoid unnecessary skin biopsies.

Several approaches have been tried to improve dermatologic diagnosis. Digital processing of reflectance images has been extensively investigated recently. Although reflectance imaging has led to improvements in the registration, recording, and documentation of skin lesions, there has been little improvement in the diagnostic accuracy. The foregoing approach does not provide any additional data to the physician making the visual assessment because it is still based on the reflectance pattern of a lesion under white light illumination which is essentially the same pattern a human observer sees.

An alternative approach is ultraviolet (UV) or infrared (IR) photography which does extend visual perception of a physician to the UV or IR reflectance patterns. However, the inconvenience due to delays in processing of film images renders this technique impractical for everyday use.

A further alternative approach that is already in widespread medical use involves a "Wood's lamp," which consists of a mercury discharge lamp associated with a filter that transmits UVA light with a 365 nanometer peak while absorbing visible light. When this device is used to assist in skin diagnosis, the eye serves as both the detector and the long pass filter. The eye is not sensitive to UV light, but is sensitive to visible fluorescence light when the "Wood's lamp" is used in a darkened room, where the physician sees an image of a fluorescing disease site. The "Wood's lamp" is useful for the diagnosis of some skin conditions such as tinea capitis, tinea versicolor, erythrasma, and some pseudomonas infections, as well as aiding in the detection and diagnosis of hypopigmented skin. It is of no value in conditions where the emitted fluorescence is not in the visible spectrum because the human eye cannot detect such fluorescence. It is also incapable of detecting Raman scattering. Thus, there has gone unmet a need for apparatus and methods that are able to detect and analyze fluorescence both within and beyond the visible spectrum, and that can use fluorescence, reflectance and/or Raman scattering to identify, and distinguish between, a variety of skin diseases.

The present invention provides these and other related advantages.

SUMMARY OF THE INVENTION

The apparatus and methods of the present invention use spectral measurements of fluorescence light, reflectance light, and/or Raman scattering from a disease site to aid in the medical assessment of skin conditions and the diagnosis of cutaneous diseases. The apparatus and methods can, if desired, be used in a normally lit room, and can distinguish between a variety of skin diseases, including actinic keratosis, basal cell carcinoma, seborrheic keratosis, compound nevus, spider angioma, psoriasis and squamous cell carcinoma.

Thus, in one aspect the present invention provides apparatus able to diagnose a disease selected from the group consisting of actinic keratosis, seborrheic keratosis, basal cell carcinoma and compound nevus at a skin disease site using spectral analysis comprising: a light source for generating light to illuminate the disease site; a probe means optically connected to the light source to expose the disease site to light to generate fluorescence and reflectance light; spectral analysis means optically connected to the probe means for generating and displaying spectral measurements of the fluorescence light and the reflectance light to assist the user in diagnosing the disease site; and a plurality of comparison spectra corresponding to, and able to distinguish between, each of actinic keratosis, seborrheic keratosis, basal cell carcinoma and compound nevus. Further preferably, in this and other aspects of the invention, the apparatus is also able to identifiably detect and diagnose spider angioma, psoriasis and/or squamous cell carcinoma. Also preferably, the apparatus is able to distinguish such diseases from actinic keratosis, seborrheic keratosis, basal cell carcinoma and compound nevus, and is further preferably able to distinguish all such diseases one from another.

In a preferred embodiment for this and other aspects of the invention, the light source comprises an excitation laser light source or other narrow band light source and a white light source, further preferably the excitation light source is a Helium-Cadmium laser and the white light source is a quartz tungsten halogen lamp.

In another preferred embodiment, the apparatus further comprises a shutter system to switch between the excitation light source and the white light source such that the disease site is illuminated sequentially by one of the light sources at a time, and a computer control means to control the shutter system by switching between light sources and to control the spectral analysis means in order to acquire spectral measurements of the fluorescence and reflectance light. The computer control means preferably comprises a personal computer and the spectral analysis means preferably comprises a computer interface card installable in an interface slot of the computer to function as a spectrometer, which computer interface card preferably includes a miniature monochromator, a CCD linear array detector, means for optically connecting to the probe means, and data acquisition and controlling circuitry.

The apparatus also preferably includes a light filter selected to pass fluorescence light and block reflected excitation light, and the light source is preferably optically connected to the probe means and the probe means is optically connected to the spectral analysis means by optical fiber bundles, further preferably including an optical coupler for connecting the white light source and the excitation light source to deliver light via the same optical fiber bundle. Still further preferably, the optical coupler comprises: an enclosure housing, an angled reflecting surface having an aperture; a laser light port in the enclosure aligned with the aperture to permit passage of laser light directly through the angled reflecting surface, the laser light port being optically connectable to a laser light source; a light exit port from the enclosure aligned with the laser light port and the aperture through the angled reflecting surface, the light exit port being optically connectable to the probe means; and, a white light port in the enclosure positioned with respect to the angled reflecting surface such that white light is reflected through an angle to be incident upon the light exit port, the white light opening being optically connectable to the white light source.

In still another preferred embodiment, the probe means comprises an elongate member having an open end defining a chamber with opaque walls that is positionable over the disease site to exclude external light from the chamber, the chamber being connected to the optical fiber bundles for receiving light from the light sources and transmitting fluorescence light and reflectance light to the spectral analysis means. Preferably, the elongate member comprises: a generally cylindrical member housing the optical fiber bundles that extend to a distal end of the cylindrical member, and a sleeve member that telescopes over the generally cylindrical housing, the overlap of the sleeve member with the distal end of the cylindrical member defining the chamber whereby slidable movement of the sleeve member with respect to the cylindrical member adjusts the length of the chamber to vary the size of the illumination spot at the disease site. Also preferably, the sleeve member is formed with a window for viewing inside the chamber to ensure proper positioning of the chamber over the disease site and a slidable cover to seal the window when the apparatus is in use, and the free end of the sleeve member is cut at substantially 45 degrees to the longitudinal axis of the sleeve to avoid specular reflection.

In another aspect, the present invention provides methods for diagnosis of a disease selected from the group consisting of actinic keratosis, seborrheic keratosis, basal cell carcinoma, compound nevus and spider angioma at a skin disease site using spectral analysis comprising the steps of: illuminating the disease site with a light source to generate fluorescence and reflectance light at the disease site; collecting the generated fluorescence and reflectance light; conducting a spectral analysis of the collected light using a spectrometer, determining spectral measurements of the fluorescence light and the reflectance light; and, examining the spectral measurements together to make a diagnosis of the disease site, wherein the step of examining comprises comparing the spectral measurements with known spectral measurements. If the reflectance curve slope is similar to normal and the fluorescence intensity is higher than normal, then determining that the disease is actinic keratosis. If the reflectance curve slope is similar to normal and the fluorescence intensity is lower than normal, then determining that the disease is basal cell carcinoma. If the reflectance curve slope is larger than normal and the fluorescence intensity is higher than normal, then determining that the disease is seborrheic keratosis. If the reflectance curve slope is larger than normal and the fluorescence intensity is lower than normal, then determining that the disease is compound nevus. If the fluorescence intensity is lower than normal and the reflectance ratio spectrum comprises a saw-tooth shape with a minimum at about 600 nm, then determining that the disease is spider angioma. If the fluorescence spectrum comprises a peak at about 630 nm–640 nm, then determining that the disease is psoriasis. If the fluorescence intensity is lower in some locations in the lesion and higher than normal other locations in the lesion, then determining that the disease is squamous cell carcinoma.

In a preferred embodiment, the steps of illuminating the disease site and collecting generated light involves sequentially illuminating the site with white light and collecting reflectance light and then illuminating the site with excitation light and collecting fluorescence light or vice versa. Also preferably, the methods include filtering the collected fluorescence light to filter out the excitation light, and a spectrometer card mounted in a personal computer is used to conduct a spectral analysis of the generated fluorescence and reflected light and display spectral measurements.

In another preferred embodiment, the step of collecting the generated fluorescence and reflectance light involves collecting light from the disease site and the surrounding normal skin. Further preferably, the step of examining the spectral measurements involves comparing the disease site spectrum to the spectrum of the surrounding normal skin, further preferably comparing the intensities of the autofluorescence spectra of the disease site and the surrounding normal skin.

In still another preferred embodiment, the step of examining the spectral measurements involves comparing the slope of the reflectance spectra of the disease site and the surrounding normal skin and/or generating a ratio spectrum by dividing the disease site spectrum by the spectrum of the adjacent normal skin.

In all aspects and embodiments of the invention, the comparison spectra are stored in a computer and the steps of comparing the various spectra or other responses are performed by a computer.

In still yet another aspect, the present invention provides systems able to diagnose a disease selected from the group consisting of actinic keratosis, seborrheic keratosis, basal cell carcinoma and compound nevus at a skin disease site using spectral analysis comprising: a light source for generating light to illuminate the disease site; an optical probe optically connected to the light source to expose the disease site to light to generate fluorescence and reflectance light; a spectral analyzer optically connected to the optical probe for generating and displaying spectral measurements of the fluorescence light and the reflectance light to assist the user in diagnosing the disease site; and a plurality of comparison spectra corresponding to, and able to distinguish between, each of actinic keratosis, seborrheic keratosis, basal cell carcinoma and compound nevus.

In still a further aspect, the present invention provides optical probes able to induce at least one of fluorescence light, reflectance light and Raman scattering in vivo in a target tissue, the optical probe comprising a proximal end, a distal end, at least one light emitting diode disposed at the distal end of the optical probe and operatively connected to a power source able to provide power to the light emitting diode such that the light emitting diode can emit excitation light able to induce at least one of fluorescence light, reflectance light and Raman scattering in the target tissue, and at least one collection fiber that transmits light from the distal end of the optical probe to the proximal end of the optical probe.

Preferably, the collection fiber is operatively connected to a spectrometer able to analyze the spectra transmitted by the collection fiber, which spectrometer is operatively connected to a memory readable by a computer that contains a plurality of comparison spectra corresponding to, and able to distinguish between, one or more of actinic keratosis, seborrheic keratosis, basal cell carcinoma and compound nevus, spider angioma, psoriasis and/or squamous cell carcinoma. Also preferably, the distal end of the optical probe comprises at least one of a plurality of light emitting diodes that emit different wavelengths of excitation light and a plurality of light filters that transmit different wavelengths of excitation light to provide a plurality of light sources, and an on and off switch to switch the light emitting diodes on and off such that the target tissue is illuminated sequentially by one of the light sources at a time. Further preferably, the probes comprise a computer that controls the on and off switch and the spectrometer in order to acquire sequential spectral measurements of at least two of fluorescence light, reflectance light and Raman scattering, which computer is typically a personal computer and the spectrometer typically comprises a computer interface card installable in an interface slot of the computer.

In still a another further aspect, the present invention provides methods for diagnosis of a skin disease using analysis of Raman scattering at a suspected skin disease site comprising the steps of: illuminating the disease site with an infrared or near-infrared light source to generate Raman scattering at the disease site; collecting the generated Raman scattering; conducting an analysis of the collected Raman scattering using a spectrometer; determining measurements of the Raman scattering; and, examining the spectral measurements together to make a diagnosis of the disease site by comparing the spectral measurements of the suspected skin disease site against measurements from a known site. Preferably, the methods comprise including filtering the collected Raman scattering to filter out the excitation light. Also preferably, the methods comprise using a spectrometer card mounted in a personal computer is used to conduct a spectral analysis of the generated Raman scattering and display spectral measurements.

In preferred embodiments, the step of collecting the generated Raman scattering involves collecting Raman scattering from the disease site and the surrounding normal skin. Further preferably, the step of examining the Raman scattering comparing the disease site Raman scattering to the Raman scattering of the surrounding normal skin, which can include comparing the intensities of the Raman scattering of the disease site and the surrounding normal skin.

In other preferred embodiments, the methods include the step of generating a ratio spectrum by dividing the disease site Raman scattering by the Raman scattering of the adjacent normal skin.

In still further aspects, the methods of the present invention comprise determining spectral measurements a 3-D spectrum of the fluorescence light. Such determination can include determining a 3-D spectrum of the fluorescence light further comprises generating a two-dimensional contour plot from the 3-D spectrum to generate a fluorescence excitation-emission matrix (EM), determining a 3-D spectrum of the fluorescence light further comprises sectioning the 3-D spectrum at a fixed emission wavelength to generate a 2-D plot of fluorescence excitation spectrum, generating a ratio matrix by dividing a 3-D spectrum from a lesion versus a 3-D spectrum from surrounding normal skin, and/or generating a subtractive matrix by subtracting a 3-D spectrum a lesion from a 3-D spectrum from surrounding normal skin.

Accordingly, the apparatus of the present invention provides apparatus for diagnosis of a skin disease site using spectral analysis comprising:

a light source for generating light to illuminate the disease site;

a probe means to conduct the illumination light from the light source to the disease site and to collect the reflected and fluorescence light and conduct said light to be analyzed; and spectral analysis means optically connected to the probe means for generating and displaying spectral measurements of the fluorescence light and the reflectance light to assist the user in diagnosing the disease site.

In a further aspect, the present invention provides a method for diagnosis of a skin disease site using spectral analysis comprising the steps of:

illuminating the disease site with a light source to generate fluorescence and reflectance light at the disease site;

collecting the generated fluorescence and reflectance light;

conducting a spectral analysis of the collected light using the spectrometer;

displaying spectral measurements of the fluorescence light and the reflectance light; and analyzing the measured fluorescence and reflectance spectra together to make a diagnosis of the disease site.

In a preferred embodiment, the apparatus of the present invention includes a compact spectrometer connected to a personal computer, a fluorescence excitation light source with a shutter, a white light source with a shutter, a bifurcated fiber bundle, a light coupler, a skin probe, and controlling electronics. The system is designed to automatically switch between the fluorescence excitation light and the white light sources and complete fluorescence and reflectance spectral measurements of a skin disease site sequentially in a few seconds. The system exploits the spectral differences of different skin diseases to aid in the dermatologic diagnosis. In particular, the apparatus provides a low costs, compact system that is capable of quickly and efficiently performing combined fluorescence and reflectance spectral analysis.

These and other aspects of the present invention will become evident upon reference to the discussion herein and the attached drawings. In addition, various references are set forth herein that describe in more detail certain procedures or apparatus, etc. (e.g., bioptomes, fluorescence technology, etc.); all such references are incorporated herein by reference in their entirety.

BRIEF DESCRIPTION OF THE DRAWINGS

Aspects of the present invention are illustrated, merely by way of example, in the accompanying drawings in which:

FIG. 9 is a schematic diagram depicting an embodiment of the present invention comprising a system for connecting a proximally-located LED light source to an illumination fiber.

FIG. 10 is a schematic diagram depicting another embodiment of the present invention comprising a system for connecting a proximally-located LED light source to an illumination fiber.

FIG. 11 depicts an end view of an array of illumination fibers disposed around a collection fiber.

FIG. 12 is a schematic diagram depicting a side view of an array of illumination and collection fibers.

FIG. 13 is a schematic diagram depicting an embodiment of the present invention comprising a system for inducing fluorescence wherein an LED is disposed at the distal end of the apparatus.

FIG. 14 is a schematic diagram depicting another embodiment of the present invention comprising an illumination apparatus wherein an LED is disposed at the distal end of the apparatus.

FIG. 15 depicts an end view of an array of illumination LEDs disposed around a collection fiber.

FIG. 16 is a schematic diagram depicting a side view of an array as set forth in FIG. 15.

DETAILED DESCRIPTION OF THE INVENTION

The present invention provides methods and apparatus relating to the induction and analysis of optical responses, such as fluorescence, reflectance, and Raman scattering, in skin in order to evaluate and diagnose diseases. The present invention provides simple and easy to use methods and apparatus for the diagnosis of such diseases, and is superior to visual examination of such disease using only white (or room) light, although the present invention is preferably used in combination with such visual examination using white light. In addition, the present invention provides details about distinguishing features that are found in a variety of skin diseases, including actinic keratosis, basal cell carcinoma, seborrheic keratosis, compound nevus, spider angioma, psoriasis and squamous cell carcinoma.

Figure 1:
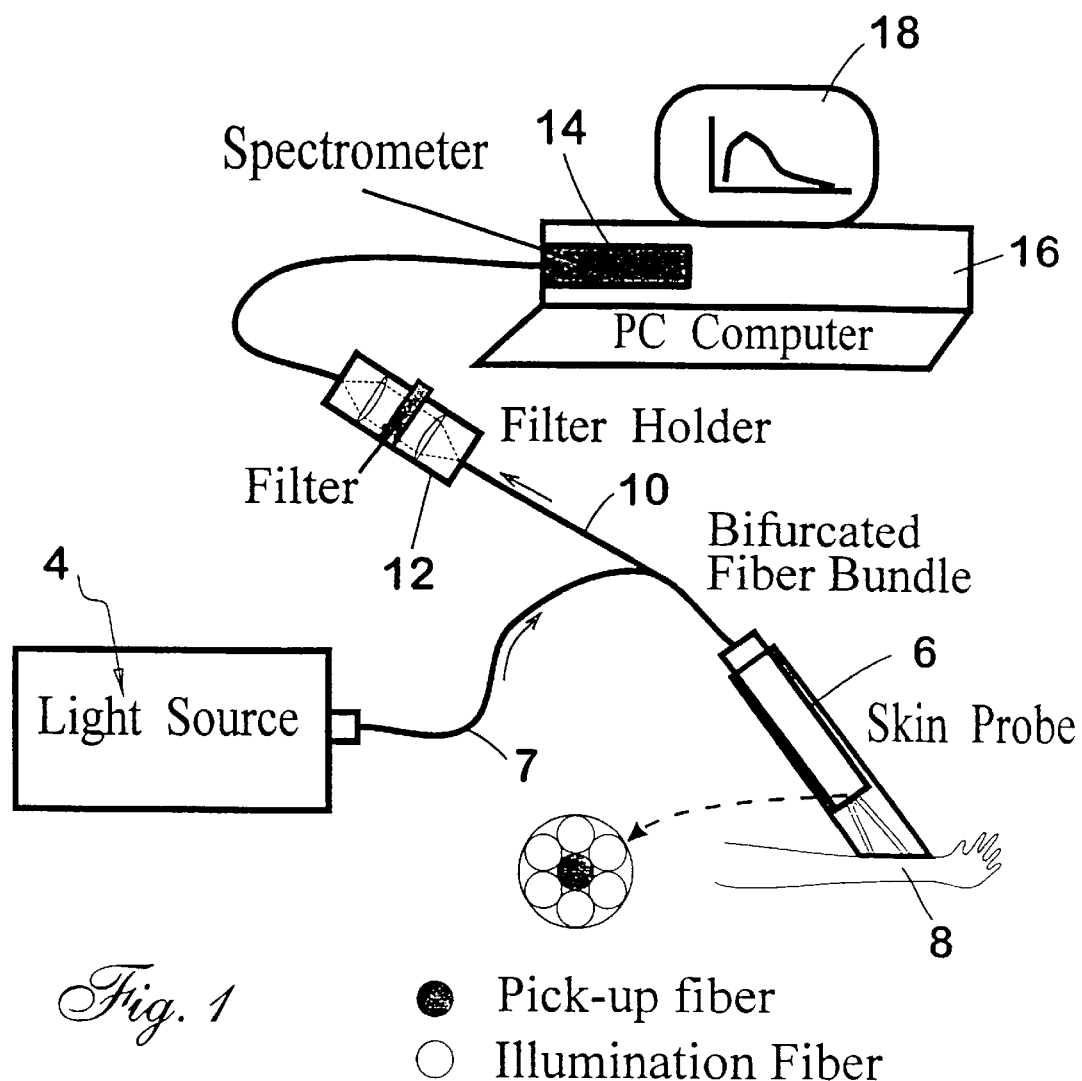
FIG. 1 is a schematic diagram showing an embodiment of the apparatus of the present invention.

Referring to FIG. 1, there is a schematic view of the apparatus of the present invention for diagnosing skin diseases. The apparatus includes a light source 4 and a probe 6 optically connected via optical fiber 7 to light source 4 for exposing a skin disease site 8 to light. The light from source 4 generates fluorescence, reflectance light and/or Raman spectra, at disease site 8 that is collected by probe 6 and transmitted by optical fiber 10 via light filter 12 to a spectral analyzer in the form of a spectrometer 14. Spectrometer 14 generates and displays spectral measurement of the fluorescence and reflectance light on the monitor 18 of a computer 16 for viewing by a user to assist in the diagnosis of the disease site.

Figure 2:
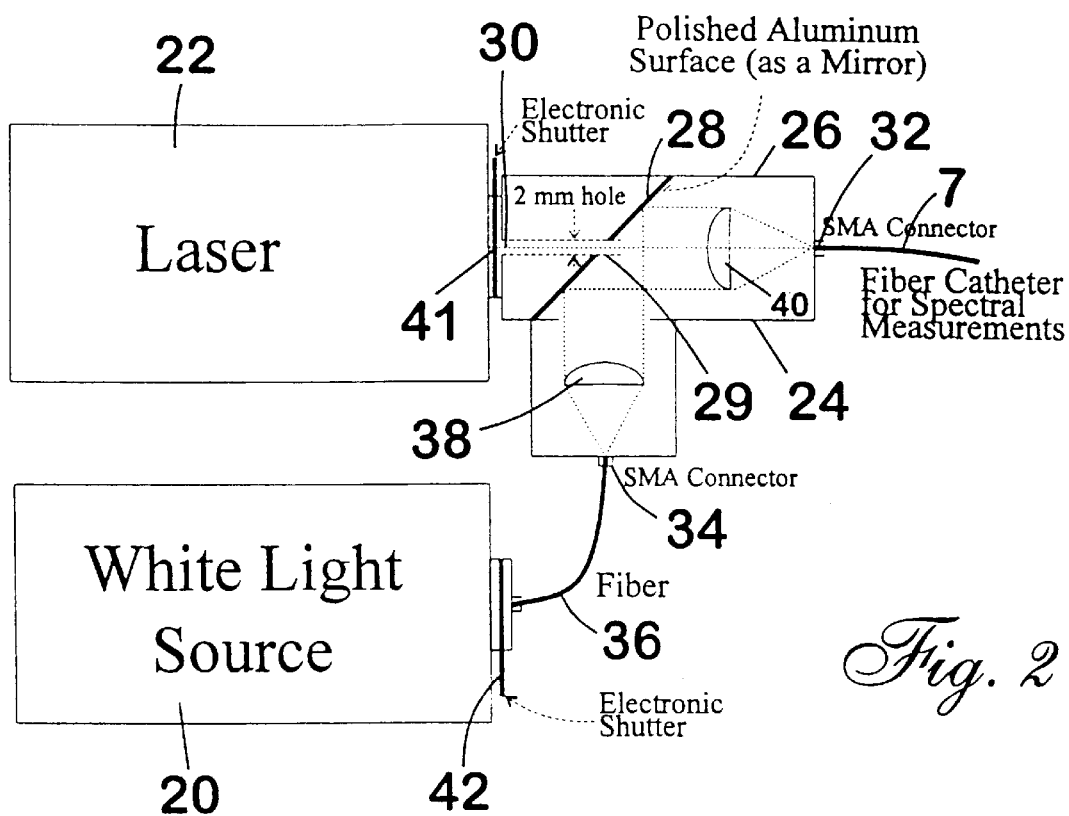
FIG. 2 is a detail view of light coupler arrangement of the present invention that connects a white light source and a laser light source.

In a preferred embodiment of the present invention, the fluorescence, reflectance and/or Raman light is acquired and analyzed sequentially. In order to accomplish this where the detected light is fluorescence and reflectance, light source 4 preferably comprises a white light source 20 for reflectance measurements as best shown in FIG. 2. Excitation light source 22 can be a Helium Cadmium (442 nm) laser and white light source 20 can be a quartz tungsten halogen lamp, where it is desired to induce a Raman scattering, the excitation light source will typically comprise an IR or near IR light source.

Turning generally to Raman spectroscopy, it detects the vibrational signatures of particular molecules inside a selected tissue, thereby providing chemical, structural and other information about the tissue. Mahavedan-Jansen, A and Richards-Kortum, R., *J Biomed Optics* 1(1): 31–70, 1996; U.S. Pat. No. 5,261,410. Raman spectroscopy of the target tissue can be used to identify particular conditions, such as those discussed herein. The wavelength bands used for determination of Raman spectra are specific to the molecules in a given tissue and provide direct information about such tissue comprising such molecules. In a preferred embodiment, similar to the gathering and comparison of fluorescence and reflectance spectra, a computer-implemented program makes use of the peak position(s) of the Raman spectrum, the relative intensities of different peaks to identify specific molecules and their relative concentrations relative to different tissue states in order to identify and distinguish one disease state from another.

In a preferred embodiment, a near NIR diode laser (e.g., $\lambda$=785 nm, 830 nm) is used for the excitation illumination. At least one excitation or illunmination light guide, such as an optical fiber, conducts the illumination light through the probe to the target tissue. Alternatively, the light source can be disposed at the distal end of the probe. At least one collection light guide then picks up the scattered light caused by the illumination light (which light includes Raman shifted photons) and then transmits the collected light to an analyzer such as a spectrometer-CCD system for spectral analysis. Preferably, two filters are located at the tip of each of the illumination light guide and the collection light guide. A band pass filter is disposed at or near the distal tip of the illumination light guide (or otherwise between the light source and the target), which filter eliminates any Raman signals generated by the illumination fiber and transmits only the excitation light to the target tissue. A long pass filter is preferably disposed at or near the tip of the collection fiber and blocks elastically scattered laser light, and passes only the Raman shifted scattered light. In a preferred embodiment, the collected light is then transmitted to a high resolution grating which is used to disperse the Raman scattered light, and then a detector such as a back-thinned CCD array is used to acquire a spectral curve. A computer, preferably a PC computer, is then used for process control and spectral data analysis.

The two light sources 20 and 22 are joined together by an optical coupler 24 that allows light from either source to be transmitted via the same optical fiber bundle 7. Optical coupler 24 comprises a sealed enclosure 26 housing an angled reflecting surface or mirror 28 having a small aperture 29. A laser light port 30 is formed in enclosure 26 to admit laser light from laser light source 22. Port 30 is aligned with aperture 29 to permit passage of laser light directly through mirror 28 to a light exit port 32 which is connectable to optical fiber bundle 7 and probe unit 6. A white light port 34 is formed in enclosure 26 and positioned with respect to mirror 28 such that white light is reflected through an angle to be incident upon light exit port 32. White light port 34 is optically connectable to white light source 20 via a short length of optical fiber 36. Lenses 38 and 40 are also provided within enclosure 26 to collimate white light from port 34 onto the mirror surface and to focus reflected light from the mirror onto light exit port 32.

Associated with each light source are shutter systems 41 and 42 to permit switching between excitation laser light source 22 and white light source 20, respectively, such that the disease site is illuminated sequentially by only one of the light sources at a time. Shutter systems 41 and 42 are preferably electronic and controlled by computer 16 (FIG. 1). Computer 16 is programmed to close shutter 41 while shutter 42 is open to obtain reflectance light measurement of the disease site and vice versa to obtain fluorescence light measurements.

In an alternative embodiment, the light source is one or more LEDs, which means a light emitting diode, including a laser-light emitting diode (laser diode) or a non-laser-light emitting diode. Using LEDs as light source(s) provides the ability to use alternative structures for the optical probe as well as alternative connections of the probe to the PC computer. It can also significantly reduce the cost of the system and can make the system more portable and more convenient to use. There are two preferred embodiments to use the LEDs as a light source: 1) coupling the LEDs to one or more optical fibers where the LEDs are disposed at a proximal end of the fiber(s), preferably where the probe has six fibers for illumination and one fiber for collection or pick-up; and, 2) placing the LEDs into the probe head (i.e., the distal end of the probe), thereby eliminating any illumination fibers but keeping the collection fiber.

FIG. 9 is a schematic diagram showing the coupling and filtering of a blue light LED to an illumination fiber for fluorescence excitation. In particular, blue LED 70 emits light peaked at 450 nm. The light is transmitted through a collimating lens or microlens 71, short pass filter 72 (which only passes light with wavelengths below 450 nm), and then focusing lens 73. Resister 74 is used to set the proper working current for the LED. 5V power supply 76 can be from a PC computer or a battery power source or other source. FIG. 10 depicts a schematic diagram that is similar to FIG. 9 and that is useful for a variety of LEDs. Thus, the diagram in FIG. 10 is lacking short pass filter 72, which filter could be incompatible with the light emitted by certain LEDs (of course, other filters, such as long pass filters or band pass filters, can be placed in the position of short pass filter 72 if desired). Multiple LEDs can be coupled to multiple fibers in this manner in order to increase the illumination power and/or provide multiple wavelengths of illumination light. For example, a blue LED, a green LED, and a red LED can be coupled to three fibers to provide full spectral illumination for reflectance measurements or other desired measurements, such as Raman responses.

FIG. 11 is a schematic diagram showing an end view of one arrangement for illumination and collection fibers at the distal end of the optical probe. R indicates an illumination fiber that is transmitting light from red LED, G indicates an illumination fiber that is transmitting light from green LED, B indicates an illumination fiber that is transmitting light from blue LED, and $B_1$, $B_2$, $B_3$ indicates three illumination fibers that are transmitting light from filtered blue LEDs. The central fiber is the pick-up or collection fiber.

FIG. 12 is a schematic diagram showing that the illumination fibers 78 can be slightly tilted toward each other as they near the distal end 52 so that light emitted from the fibers will be co-centered at a desired point of the potential skin disease site 8. This arrangement assists each illumination fiber 78 to launch its light onto the same area as much as possible. This can be particularly helpful in systems where each illumination fiber carries light having different wavelengths. FIG. I shows an arrangement suitable for use with the modified spectrometer system shown in FIGS. 9–12, except that the light source would be an LED light source. The switching between the LED illumination for fluorescence excitation, reflectance measurement and/or Raman response induction or measurement can be effected by turning the power on or off with respect to the various LEDs.

Turning to another embodiment, FIG. 13 is a schematic diagram showing a system wherein the light is emitted by a distally-located blue LED 70, which light is collimated by a collimating microlens 71 and then filtered by a short pass filter 72 to transmit the illumination to the skin for fluorescence excitation. FIG. 14 is a schematic diagram showing light from a distally-located LED that can be other than a blue LED, and thus lacking short pass filter 72 which could be incompatible with the light emitted by a given LED (of course, other filters, such as long pass filters or band pass filters, can be placed in the position of short pass filter 72 if desired). Multiple LEDs can be used in order to increase the illumination power and/or provide multiple wavelengths of illumination light. Thus, a blue LED, a green LED, and a red LED can be used to provide full spectral illumination for reflectance measurements or other desired measurements, such as Raman responses.

Figure 17:
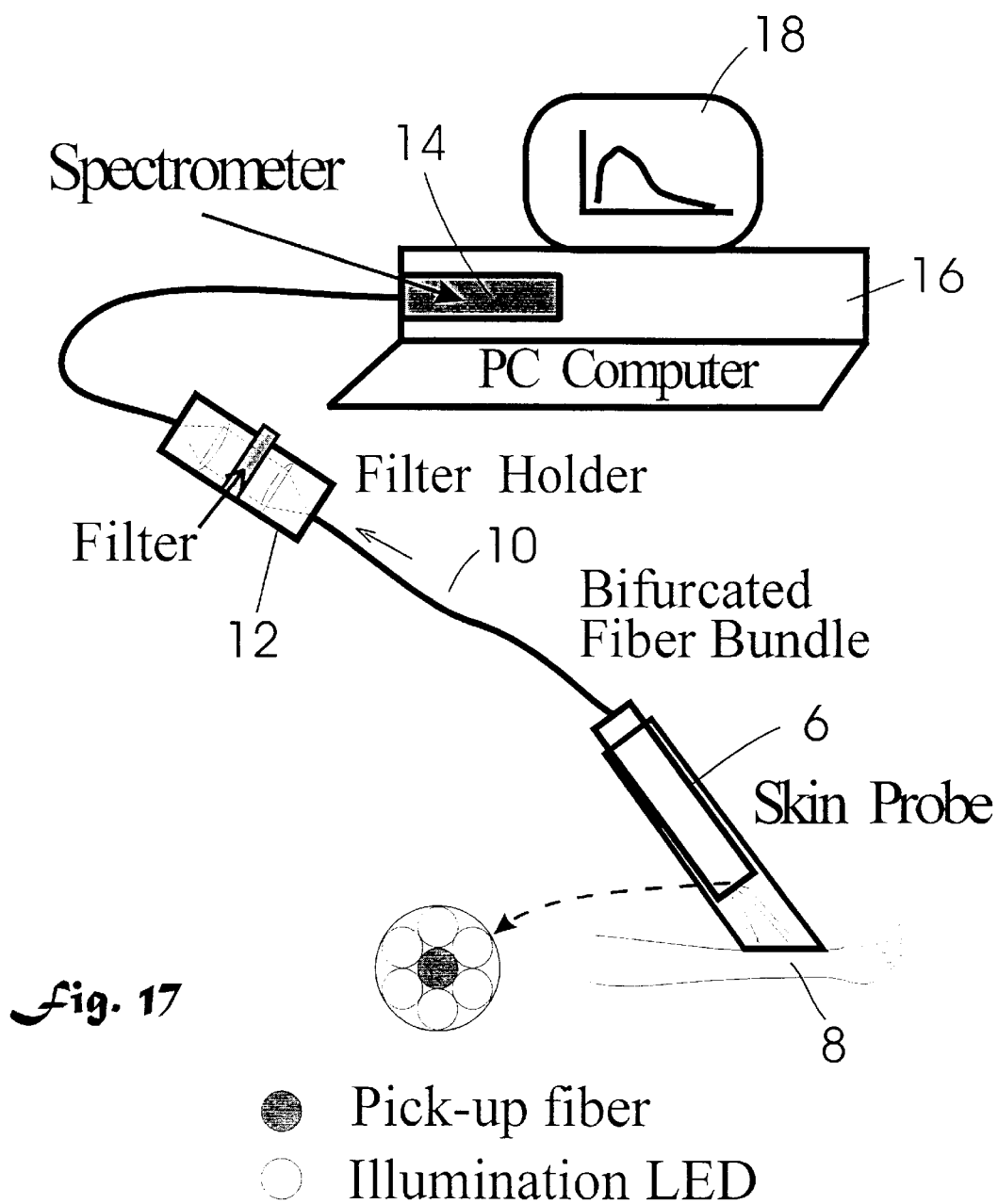
FIG. 17 is a schematic diagram showing an embodiment of the apparatus of the present invention that is similar to the apparatus set forth in FIG. 1 except that the proximally located light source has been removed.

FIG. 15 shows an arrangement of the LEDs relative to the collection fiber that is similar to the arrangement set forth in FIG. 11, except that the LEDs are located at the distal end of the probe. FIG. 16 is a schematic diagram showing an LED assembly wherein the LEDs 70 are slightly tilted toward each other and a collection fiber 80 at the distal end 52 of an optical probe 6 and co-centered at a central point of a potential skin disease site 8. This arrangement enhances the ability of the LEDs to illuminate the same area of potential skin disease site 8. FIG. 17 is a schematic diagram showing a system that is similar to that set forth in FIG. 1, except that light source 4 has been eliminated because the LEDs are disposed at the distal end of probe 6.

Figure 3:
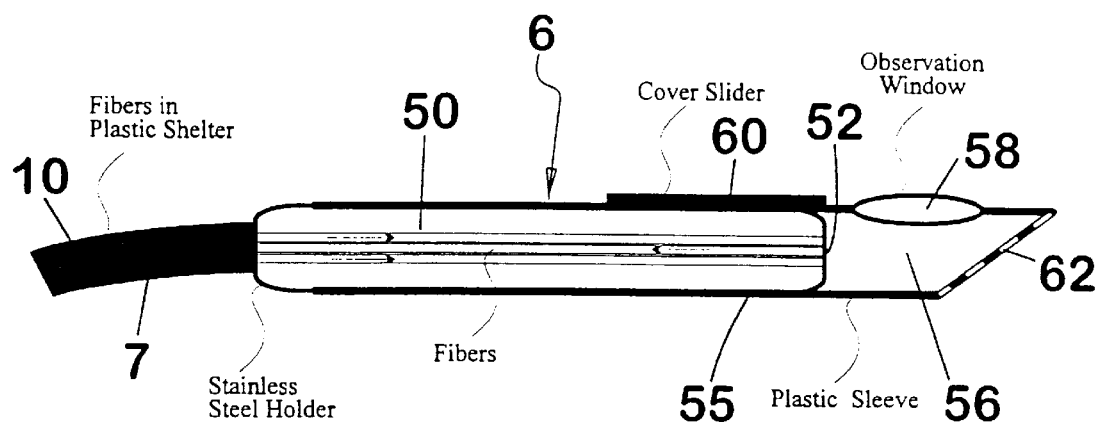
FIG. 3 is a detail section view of the probe member according to a preferred embodiment of the present invention.
Figure 4A:
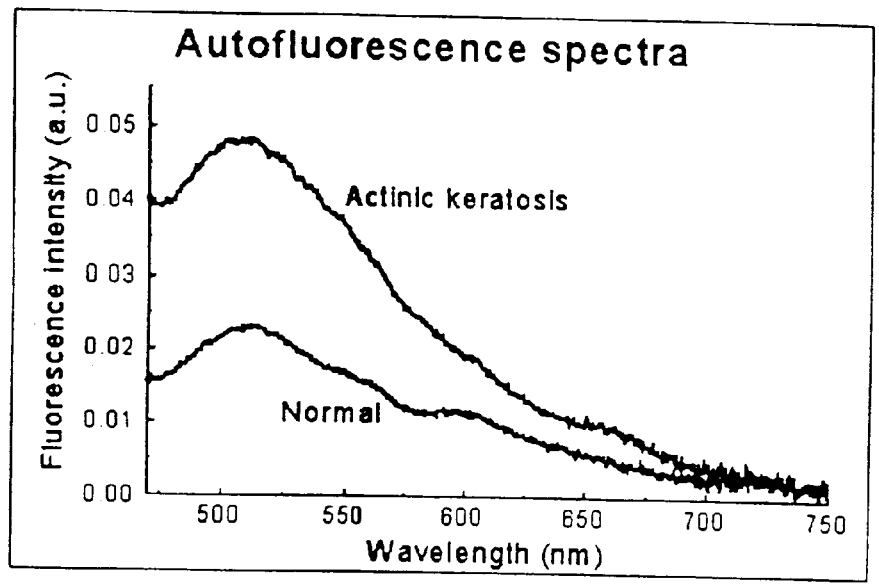
FIG. 4a to 4h are fluorescence and reflectance spectral measurements of various skin diseases that illustrate how viewing both spectral measurements together assists a user in identifying a particular skin disease.
Figure 4B:
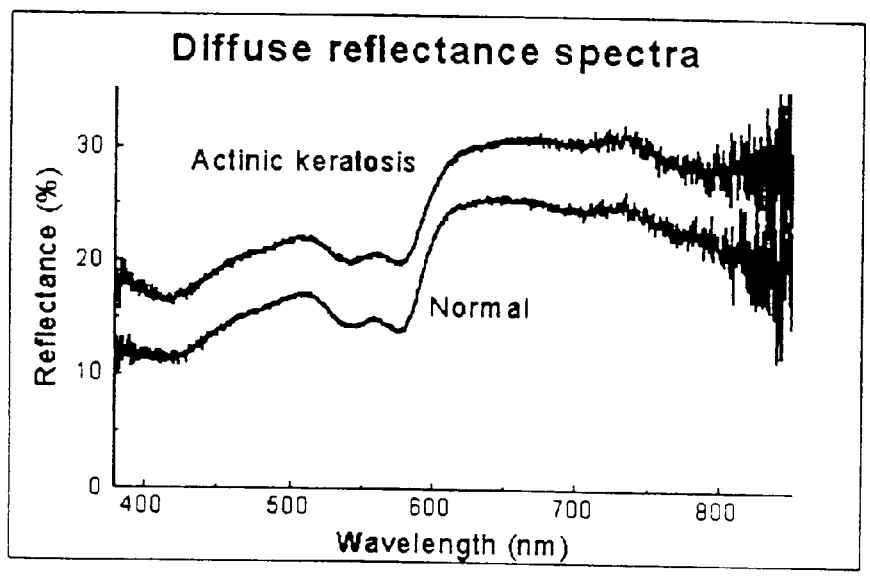
Figure 4C:
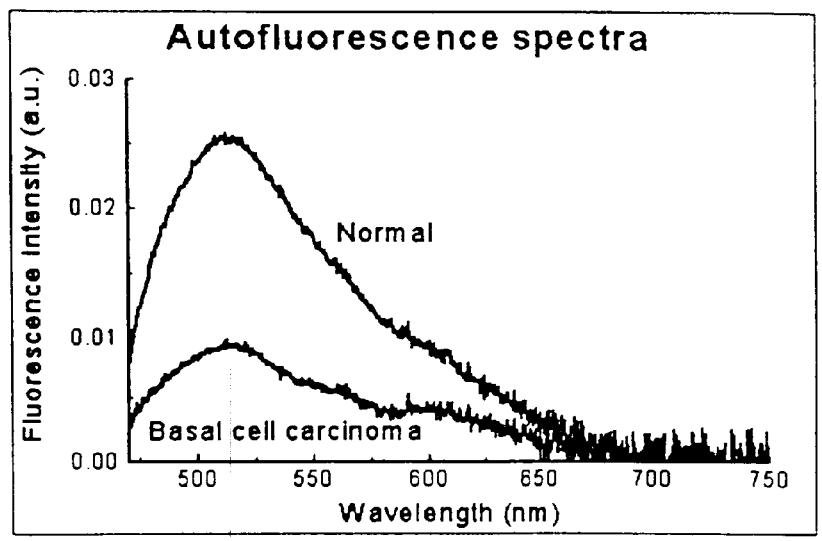
Figure 4D:
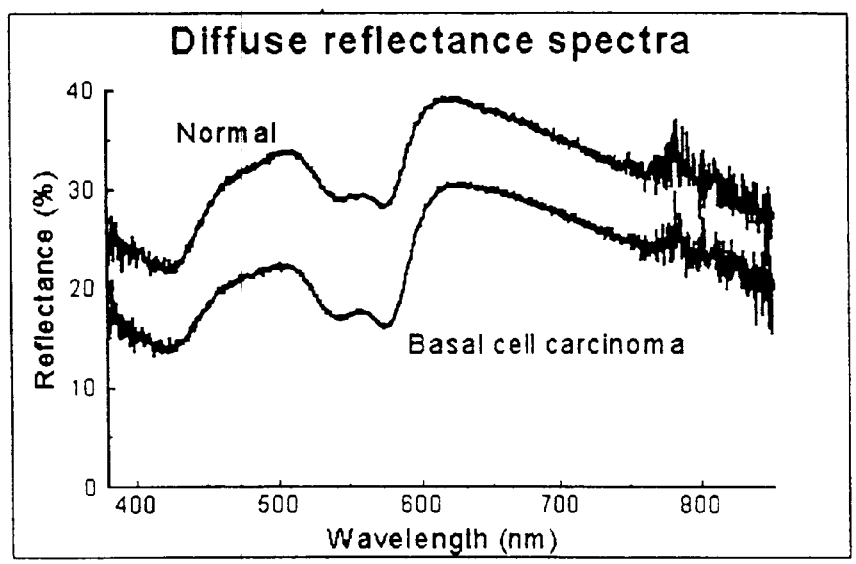
Figure 4E:
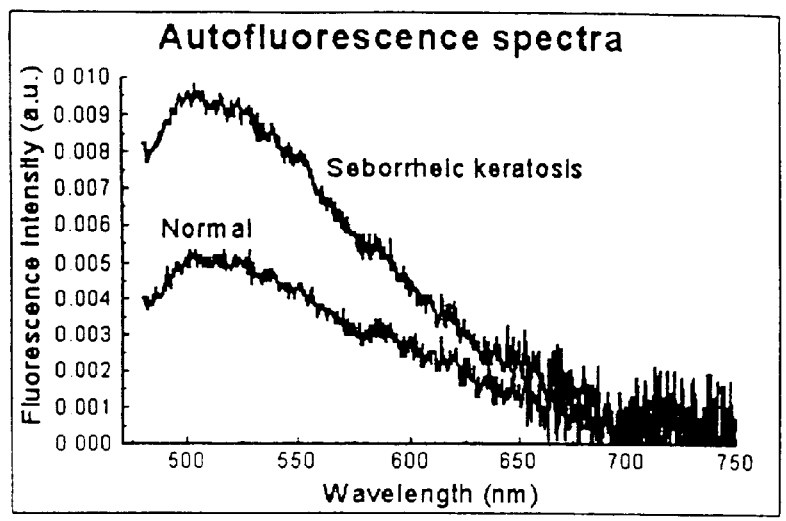
Figure 4F:
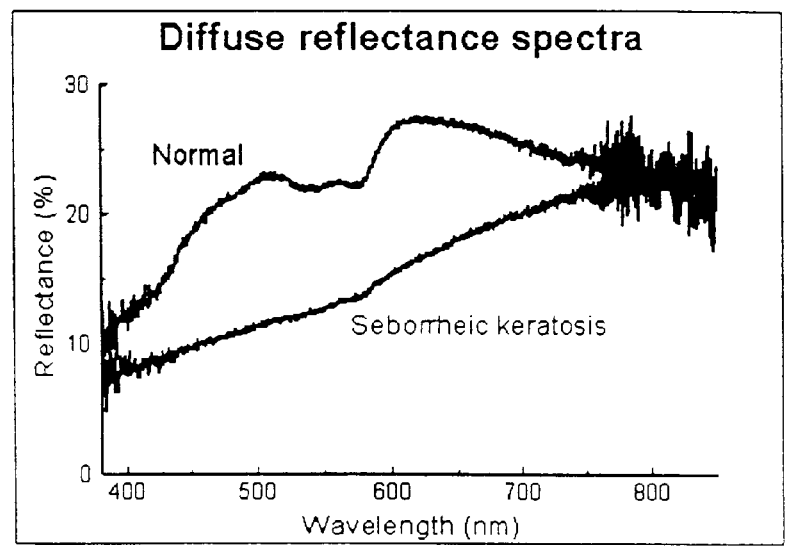
Figure 4G:
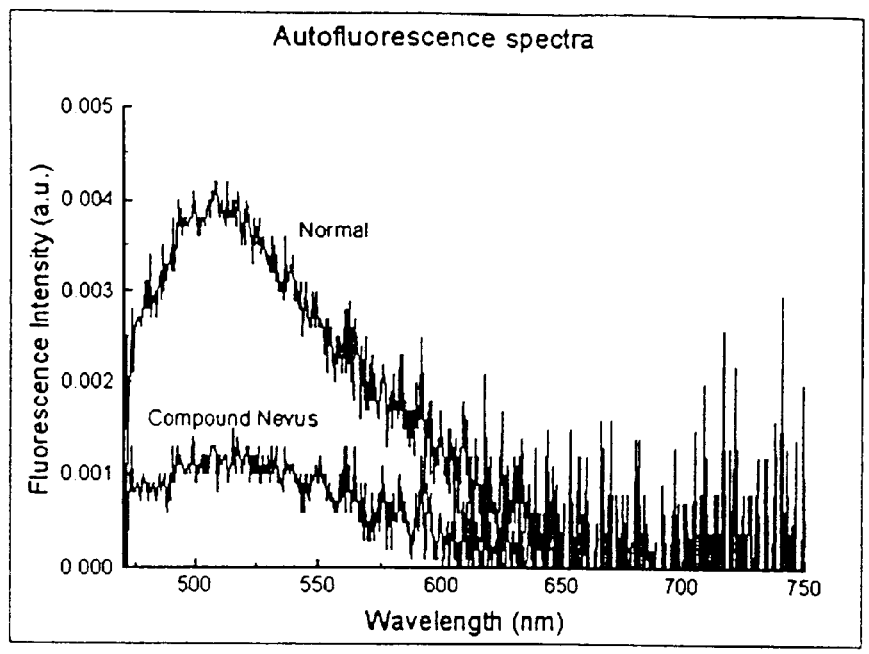
Figure 4H:
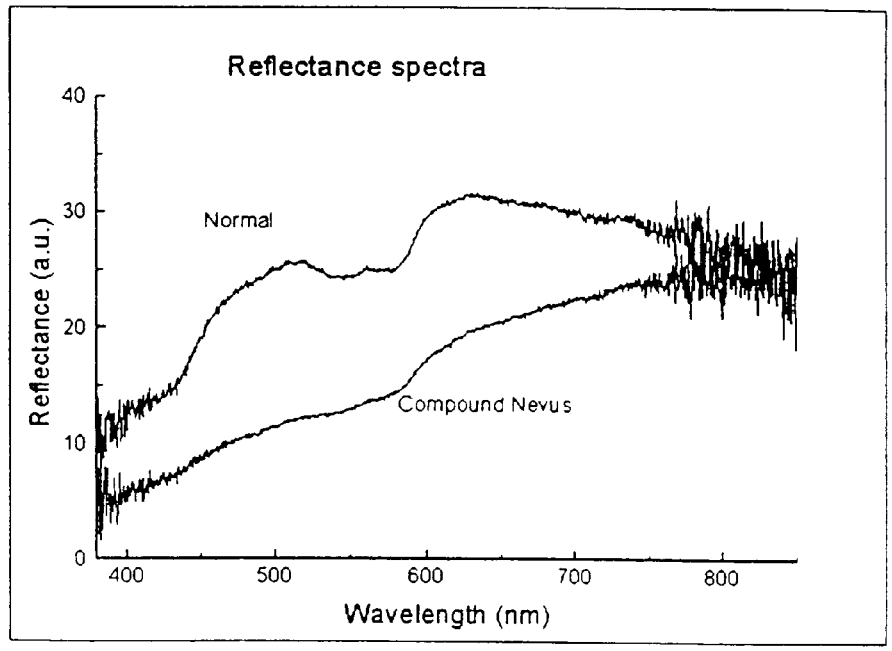

FIG. 3 is a detailed view of a probe unit 6 used to illuminate disease site 8 with light from the light sources and collect fluorescence, reflectance or other light from the site to transmit to spectrometer 14. Probe unit 6 comprises a generally cylindrical member 50 that houses combined optical fiber bundles 7 and 10 that extend to a distal end 52 of the cylindrical member. An opaque sleeve member 55 is telescopically mounted on cylindrical member 50 for slidable movement. The overlap of sleeve member 55 with distal end 52 of cylindrical member 50 defines a chamber 56 that is positionable over skin disease site 8 of interest. Fiber bundle 7 communicates with chamber 56 to transmit illumination light into the chamber and fiber bundle 10 communicates with the chamber to transmit fluorescence, reflectance or other light from the chamber to the spectrometer 14.

Slidable movement of sleeve member 55 with respect to cylindrical member 50 adjusts the length of chamber 56 and hence the distance between the fiber bundles at distal end 52 to vary the size of the illumination spot at disease site 8. By adjusting the length of chamber 56, different sizes and areas of disease sites can be examined and diagnosed.

Free end 62 of sleeve member 56 is preferably cut at a 45 degree angle to the longitudinal axis of the sleeve. This avoids the collection of specular reflected light from the skin surface. In addition, sleeve member 55 is preferably formed with a window 58 to allow observation inside the chamber when positioned over a disease site to ensure proper positioning. There is a slidable cover 60 to seal the window when the apparatus is in use. The design of probe unit 6 is such that the apparatus of the present invention can be used in a normally lighted room since no ambient light is able to enter chamber 56 and interfere with spectral measurement when chamber 56 is positioned over a disease site and cover 60 is closed over window 58.

The small cross-sectional area of sleeve member 55 is all that actually contacts the skin at disease site 8 in order to minimize the pressure on the disease site. Any excessive pressure on the skin at the disease site will affect the blood content in the skin tissue at the disease site which will affect the resulting spectral measurements.

Light collected from the sample site, which can be, for example, fluorescence light, reflectance light or Raman scattering, is transmitted via optical fiber 10 to spectrometer 14. When it is desired to collect fluorescence light or Raman scattering, shutter 41 is open to transmit excitation laser light to the disease site, filter 12 is used to pass fluorescence light or Raman scattering to the spectrometer and block any reflected excitation light. For example, if a He-Cd laser is used to generate an excitation light of 442 nm wavelength, a 470 nm long pass filter 12 will pass fluorescence light with wavelengths larger than 470 nm but will block reflected excitation light.

Preferably, spectrometer 14 is a computer interface card installable in an interface slot of computer 16 which is preferably a standard personal computer (PC) having an I/O bus appropriate to receive the interface card. Such a PC based plug-in spectrometer is available from Ocean Optics, Inc. (Dunedin, Fla.) under the name Model PC 1000. The plug-in spectrometer is adapted to connect to optic fiber 10 and includes a miniature monochromator, a CCD linear array detector, and all data acquisition and controlling electronics on the interface card. A spectrometer version for laptop computers using a PCMCIA port may also be used.

As previously described, computer 16 controls shutter systems 41 and 42. The computer can also control the LEDs by turning them on or off Computer 16 also controls spectrometer 14 in order to acquire spectral measurements of the fluorescence, reflectance or other light from the disease site. In prototype testing, the necessary spectral measurements of fluorescence and reflectance light were accomplished in a few seconds.

FIGS. 4a to 4h illustrate typical fluorescence and reflectance spectra of particular skin diseases acquired using the apparatus and methods of the present invention. Using reflectance spectra alone or visual inspection of white light illumination, it can be difficult to differentiate between various skin conditions such as seborrheic keratosis (FIG. 4f) and compound nevus (FIG. 4h), or between actinic keratosis (FIG. 4b) and basal cell carcinoma (FIG. 4d) since each pair of skin diseases have similar reflectance spectra. However, when a user also considers the corresponding fluorescence spectrum for the particular skin disease, it is possible to differentiate between seborrheic keratosis (FIG. 4e) with a fluorescence intensity higher than normal skin and compound nevus (FIG. 4g) with fluorescence intensity much lower than normal skin. In a similar manner, it is possible to use fluorescence spectra to differentiate between actinic keratosis (FIG. 4a) with a fluorescence intensity higher than normal skin and basal cell carcinoma (FIG. 4c) having a fluorescence intensity lower than normal skin.

It is important to note that he apparatus and method of the present invention rely on using both reflectance and fluorescence spectral measurements in combination to assist in diagnosis. In general, comparing only one type of spectral measurements results in difficulties in distinguishing between certain skin diseases. For example, using only fluorescence spectra for each skin disease makes it difficult to distinguish between actinic keratosis (FIG. 4a) and seborrheic keratosis (FIG. 4e) or between basal cell carcinoma (FIG. 4c) and compound nevus (FIG. 4g) as each of these particular pairs of skin diseases have similar fluorescence spectra. The fact that the above pairs of skin diseases have different reflectance spectra allow them to be distinguished clearly from each other.

TABLE 1

Distinguishing between skin conditions by considering fluorescence and reflectance spectral characteristics

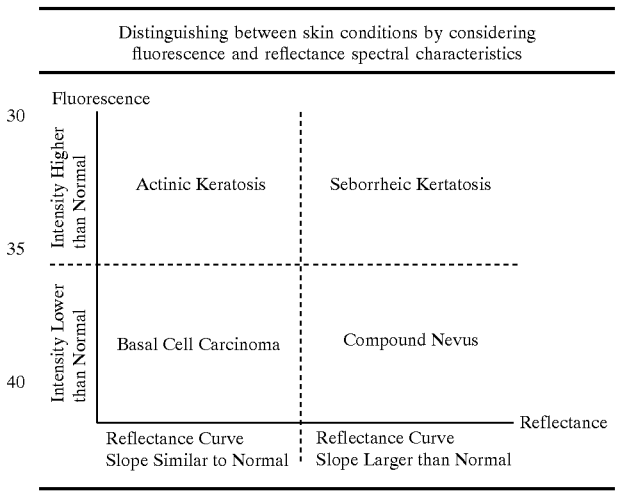

Figure 5:
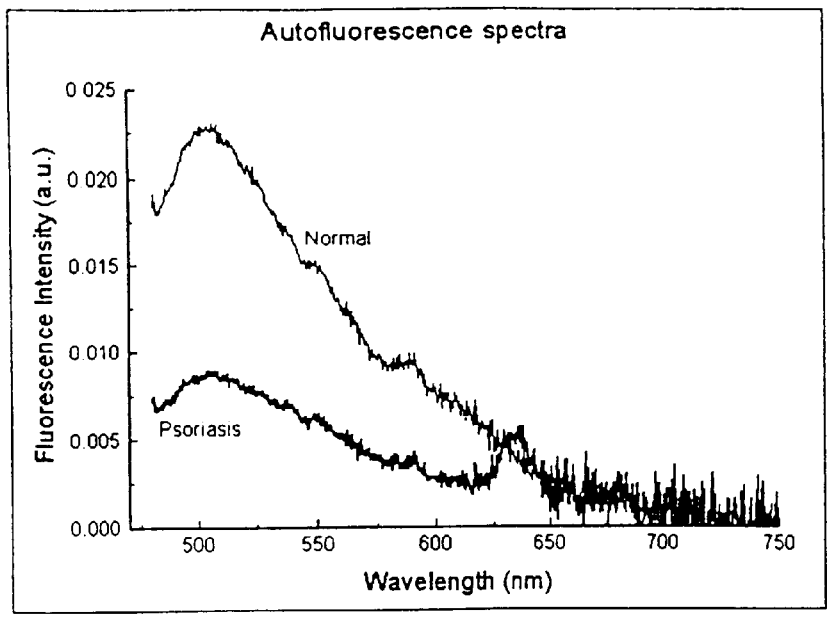
FIG. 5 is a fluorescence spectrum of a psoriasis lesion.
Figure 6:
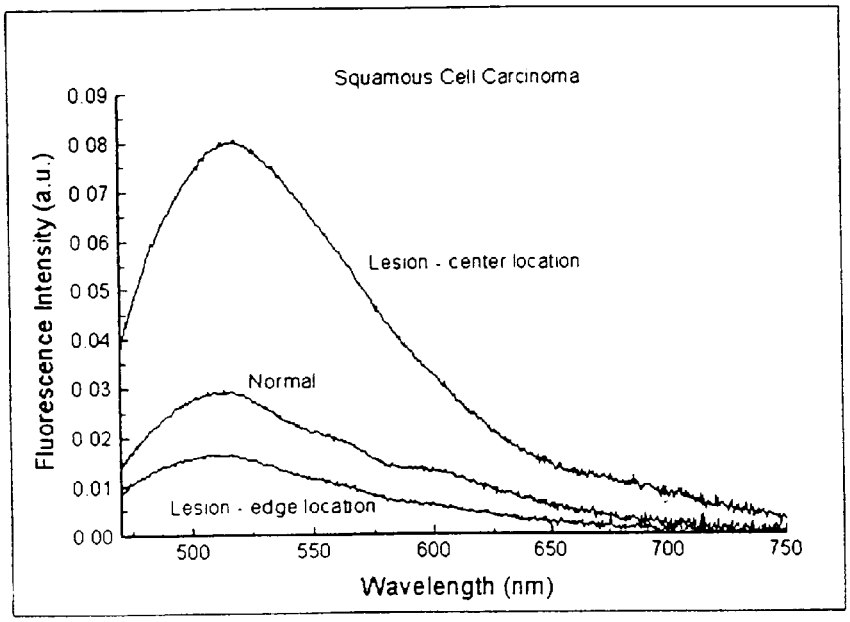
FIG. 6 is a fluorescence spectrum of a squamous cell carcinoma (SCC).

More sample spectra are shown in FIGS. 5–8. FIG. 5 is the fluorescence spectrum of a psoriasis lesion, showing a unique spectral peak at around 635 nm that allows psoriasis to be differentiated from other skin lesions. FIG. 6 shows fluorescence spectra of a squamous cell carcinoma (SCC). The fluorescence intensity across a SCC lesion is not uniformly distributed. As shown, in some places within the lesion the fluorescence intensity is higher than normal skin, while in other locations the fluorescence intensity is lower than normal. This feature for SCC lesions is different from that of basal cell carcinomas (BCC), where the fluorescence intensity is uniformly lower than found in surrounding normal skin.

It is important to compare lesional spectra to the spectra of the surrounding normal skin in order to assess the spectral features of diseased skin. This comparison compensates for the regional variations in skin optical properties and spectral features. It also adjusts for intersubject variability.

To further standardize the method of the present invention, we have developed a ratio technique to aid spectra interpretation. In the ratio analysis technique, lesional spectra (reflectance or fluorescence) are divided by the corresponding spectra of the surrounding normal skin. In this way, the relative spectral intensity changes are quantified, and the spectral shape changes are enhanced and more easily visualized on the spectral curves.

FIG. 7 shows the original spectra and the ratio spectra of a seborrheic keratosis. FIG. 7a is the original fluorescence spectra, the lesion has higher fluorescence intensity than the normal, but the shape of the two curves are visually about the same. FIG. 7b is the fluorescence ratio spectrum which equals the lesion fluorescence spectrum divided by the normal fluorescence spectrum. The absolute value of the ratio spectrum is larger than 1, indicating that the lesion has higher fluorescence intensity than the normal and it indicating quantitatively how many times higher the lesion signal is than the normal at each wavelengths. Interestingly, a valley around 510 nm is shown on the ratio spectrum curve, which valley is unique to seborrheic keratosis and cannot be discerned by only looking at the original spectra shown in FIG. 7a. Therefore, using the ratio technique, new spectral features have been revealed from the original spectra and new diagnostic information has been obtained.

Figure 7A:
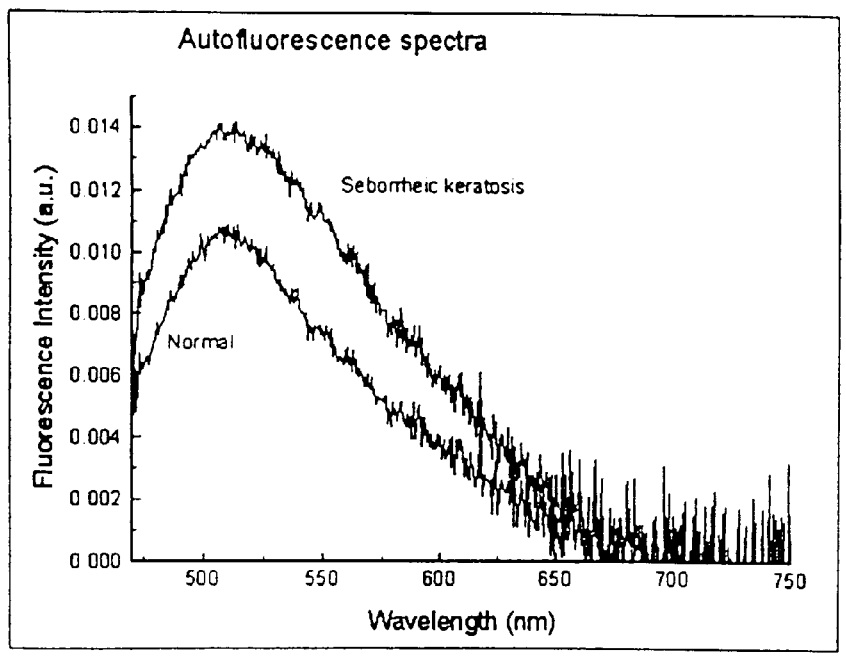
FIG. 7a shows the fluorescence spectra of normal skin and seborrheic keratosis.
Figure 7B:
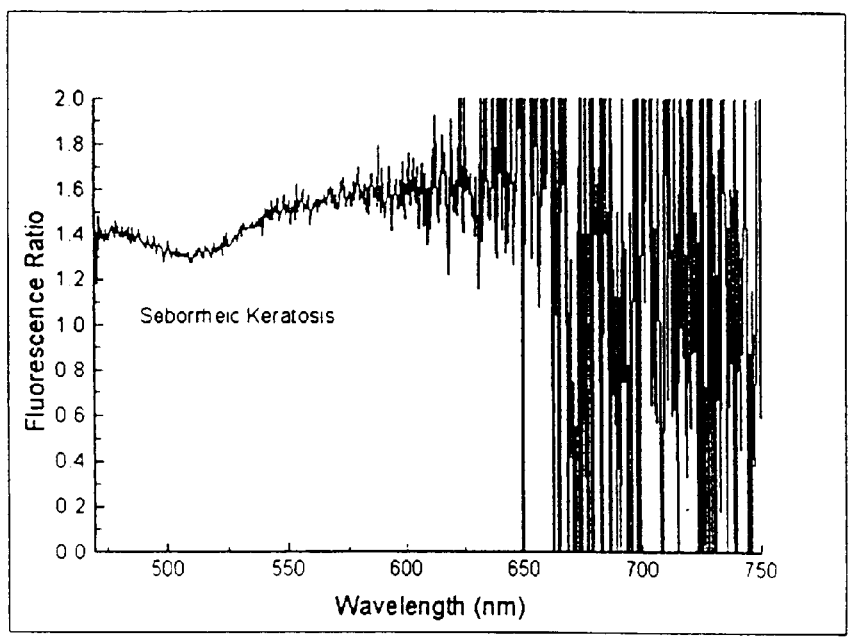
FIG. 7b shows the fluorescence ratio spectrum of seborrheic keratosis equal to the lesion fluorescence spectrum divided by the normal skin fluorescence spectrum.
Figure 7C:
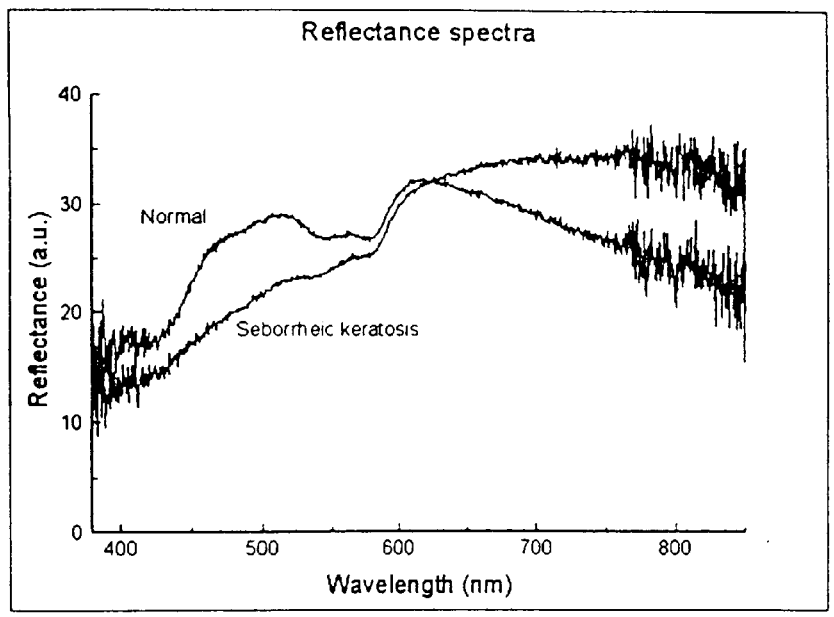
FIGS. 7c and 7d show the reflectance spectra and reflectance ratio spectrum, respectively, of seborrheic keratosis.
Figure 7D:
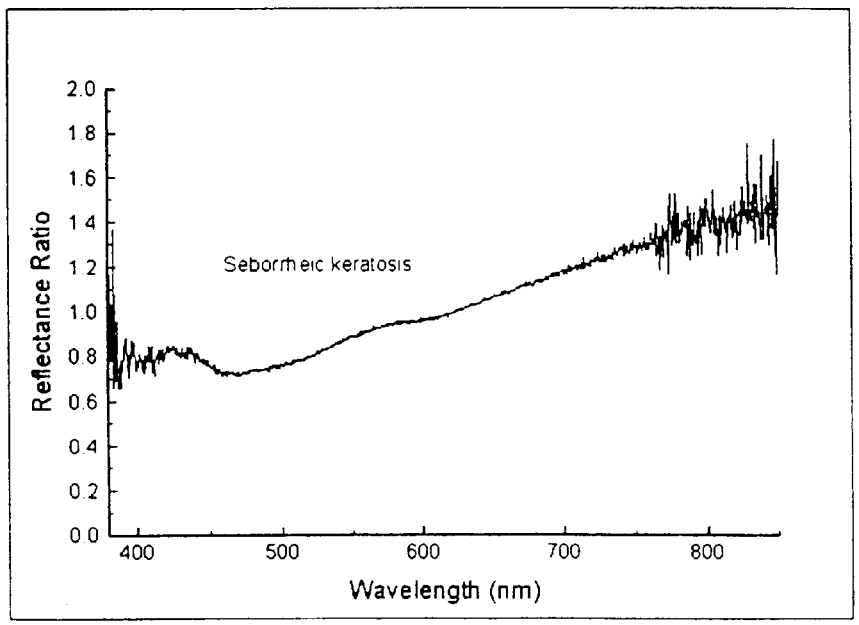

FIG. 7c is the reflectance spectra of the same seborrheic keratosis lesion and its surrounding normal skin. FIG. 7d is the reflectance ratio spectrum which equals the lesion reflectance spectrum divided by the normal reflectance spectrum. The reflectance ratio spectrum of seborrheic keratosis shows lower values at short wavelengths and higher values at longer wavelengths and is a quantitative representation of the slope changes described in Table 1.

Figure 8A:
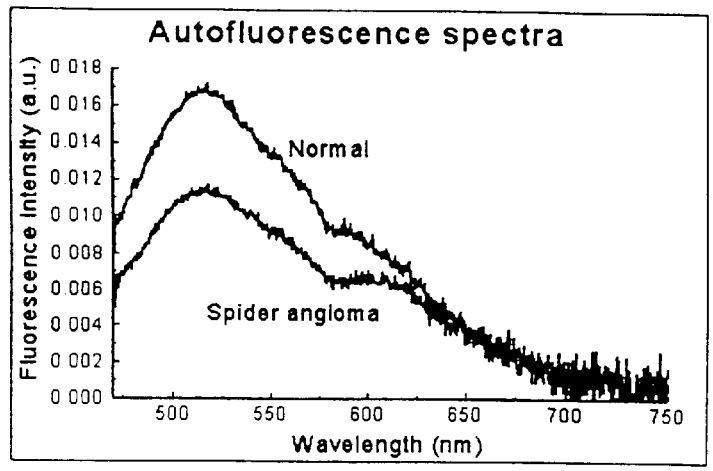
FIG. 8a shows the fluorescence spectra of spider angioma and normal skin.
Figure 8B:
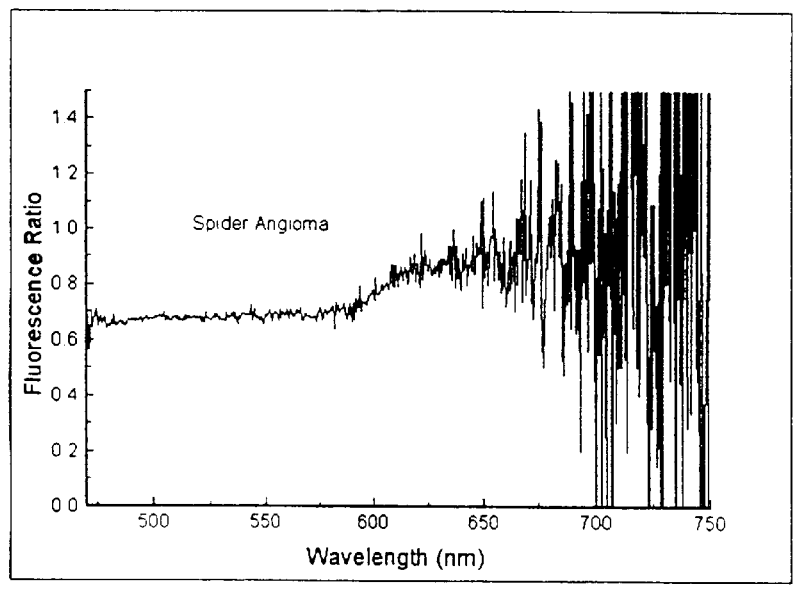
FIG. 8b shows the fluorescence ratio spectrum of spider angioma equal to the lesion fluorescence spectrum divided by the normal skin fluorescence spectrum.
Figure 8C:
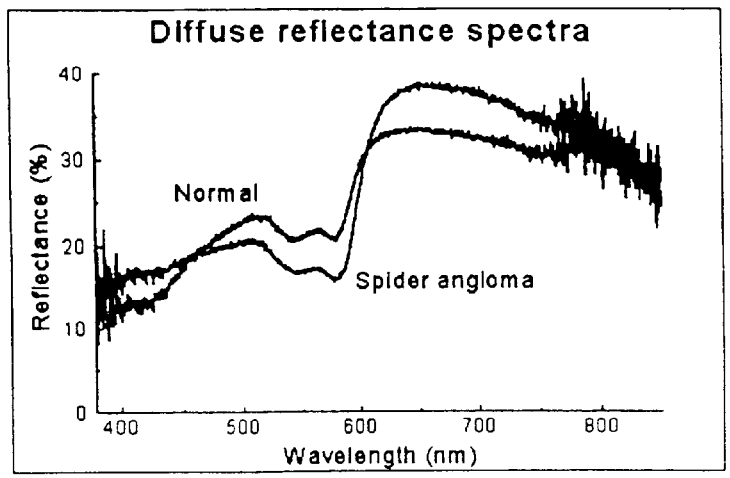
FIG. 8c and 8d show the reflectance spectra and reflectance ratio spectrum, respectively, of spider angioma.
Figure 8D:
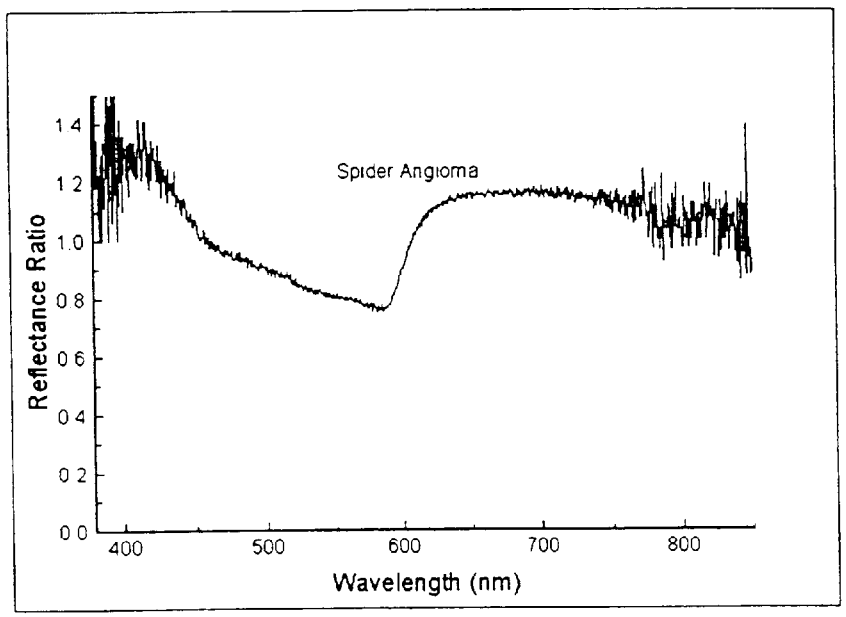

FIG. 8a is the fluorescence spectra of a spider angioma and its surrounding normal skin. The lesion has lower fluorescence intensity than normal skin. FIG. 8b is the fluorescence ratio spectrum of the same lesion. The ratios with values less than 1 indicate that the lesional fluorescence intensity is lower than its surrounding normal skin while the numerical ratio values quantify this difference as a function of wavelength. FIG. 8c shows the reflectance spectra of the same spider angioma, and FIG. 8d the reflectance ratio spectrum. The reflectance ratio spectra of spider angiomas have a unique "saw-tooth" shape with a minimum at around 600 nm. This unique spectral feature can be used to differentiate spider angioma from other skin lesions.

In another embodiment, autofluorescence spectra collected at many different excitation wavelengths can be used to build a 3-D spectral diagram. In this diagram, the X-axis is the excitation wavelength, the Y-axis is the emission wavelength, and the Z-axis is the fluorescence intensity. 3-D spectra provide more information than a single spectral curve obtained with a single excitation wavelength. The specific patterns of 3-D spectra permit accurate diagnosis of skin diseases.

Figure 18:
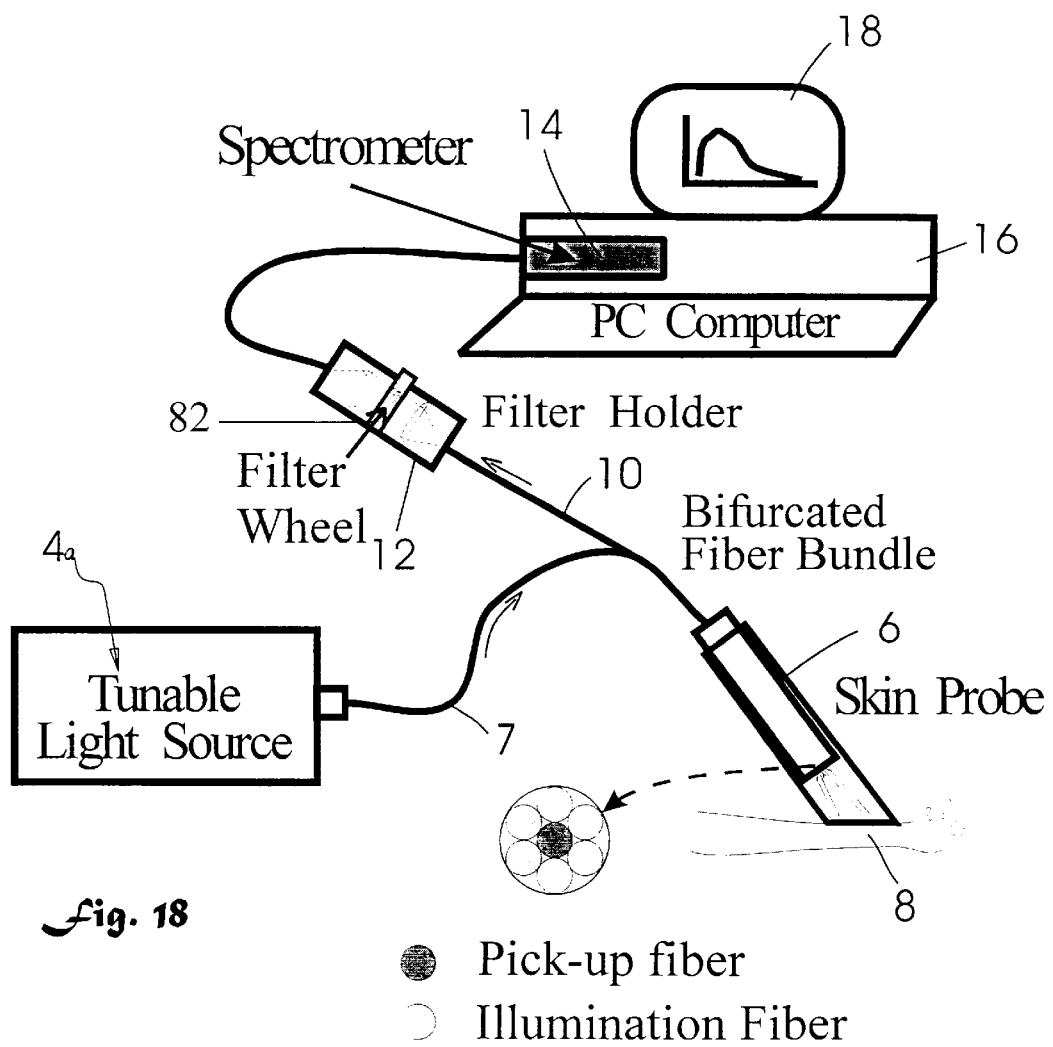
FIG. 18 is a schematic diagram showing an embodiment of the apparatus of the present invention that is similar to the apparatus set forth in FIG. 1 wherein that the proximally located light source is a tunable light source.

FIG. 18 is a schematic diagram showing a spectrometer system for such 3-D measurements. It is similar to the system set forth in FIG. 1 except that a tunable light source 4a is used to provide different excitation wavelengths for fluorescence excitation (or other desired response such as reflectance or Raman scattering), and the long pass filter in the in-line filter holder is replaced with a filter wheel 82 holding multiple, different long pass filters (or other filters for non-fluorescent uses). When the excitation wavelength changes, the wheel switches to different long pass filters. The tunable light source 4a can be, for example, a Xenon arc lamp-monochromator combination, a nitrogen dye laser system, or an OPO (optical parameter oscillator).

Figure 19:
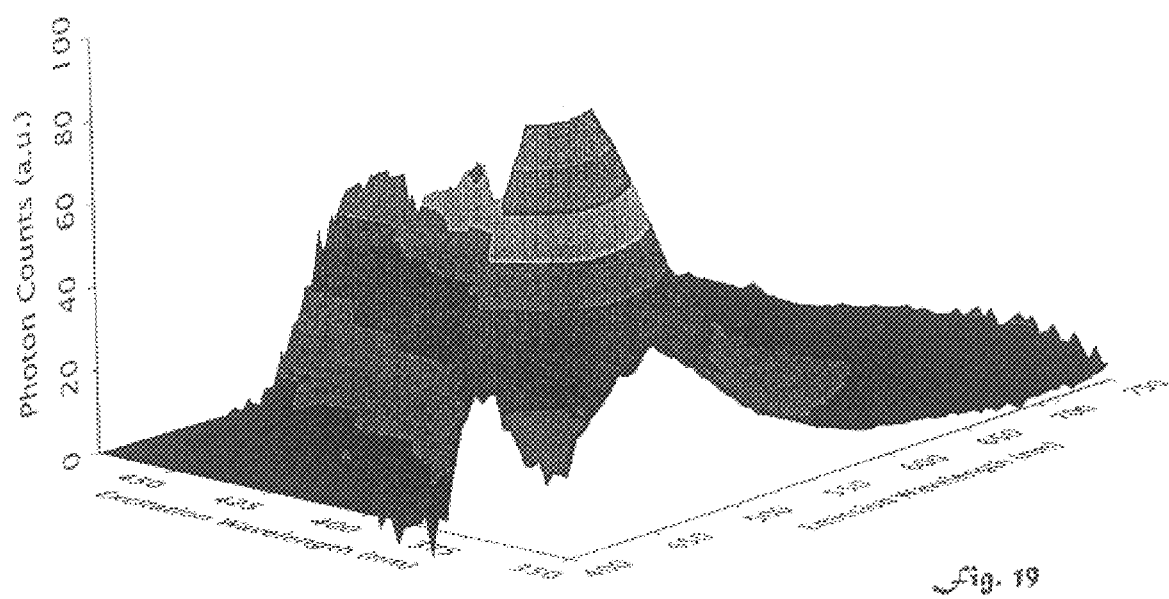
FIG. 19 depicts a 3-D autofluorescence spectrum from a normal skin site.

FIG. 19 shows an example of a 3-D autofluorescence spectrum obtained from a normal skin site. There are maximum peaks at the excitation-emission wavelengths (i.e., 380 nm, 470 nm). This type of 3-D spectrum shows different spectral characteristics for different skin diseases including skin cancer, and therefore aids the dermatology diagnosis. Two preferred methods of analyzing the 3-D data include (1) making a two-dimensional contour plot of FIG. 19 to generate a so-called fluorescence excitation-emission matrix (EEM), and/or (2) sectioning the 3-D graph at a fixed emission wavelength to generate a 2-D plot called a fluorescence excitation spectrum. From the excitation spectrum, one can observe the absorption properties of specific fluorophores. In addition, the spectra can be analyzed using a 3-D fluorescence matrix wherein derivatives of the "raw" 3-D matrix are generated. Examples of such derivatives include "ratio" matrices generated by dividing a spectrum from a lesion versus a spectrum from (preferably surrounding) normal skin, and "subtractive" matrices generated by subtracting a spectrum a lesion from a spectrum from (preferably surrounding) normal skin.

Although the present invention has been described in some detail by way of example for purposes of clarity and understanding, it will be apparent that certain changes and modifications may be practiced within the scope of the appended claims.

What is claimed is:

1. An optical probe able to induce at least one of fluorescence light, reflectance light and Raman scattering in vivo in a target tissue, the optical probe comprising a proximal end, a distal end, at least one light emitting diode disposed at the distal end of the optical probe and operatively connected to a power source able to provide power to the light emitting diode such that the light emitting diode can emit excitation light able to induce at least one of fluorescence light, reflectance light and Raman scattering in the target tissue, and at least one collection fiber that transmits light from the distal end of the optical probe to the proximal end of the optical probe, the distal end of the optical probe comprising at least one of a plurality of light emitting diodes that emit different wavelengths of excitation light and a plurality of light filters that transmit different wavelengths of excitation light to provide a plurality of light sources, and an on and off switch to switch the light emitting diodes on and off such that the target tissue is illuminated sequentially by one of the light sources at a time.

2. An optical probe as claimed in claim 1 in which the collection fiber is operatively connected to a spectrometer able to analyze the spectra transmitted by the collection fiber, which spectrometer is operatively connected to a memory readable by a computer that contains a plurality of comparison spectra corresponding to, and able to distinguish between, each of actinic keratosis, seborrheic keratosis, basal cell carcinoma and compound nevus.

3. An optical probe as claimed in claim 2 further comprising a computer that controls the on and off switch and the spectrometer in order to acquire sequential spectral measurements of at least two of fluorescence light, reflectance light and Raman scattering.

4. An optical probe as claimed in claim 3 in which the computer comprises a personal computer and the spectrometer comprises a computer interface card installable in an interface slot of the computer.

5. An optical probe as claimed in claim 4 in which the spectrometer computer interface card includes a miniature monochromator, a CCD linear array detector, and data acquisition and controlling circuitry.

6. An optical probe as claimed in claim 1 in which the collection light guide comprises a light filter selected to pass fluorescence light and block reflected excitation light.

7. An optical probe as claimed in claim 1 in which the optical probe is optically connected to the spectrometer by optical fiber bundles.

8. An optical probe as claimed in claim 1 in which the optical probe comprises an elongate member having an open end defining a chamber with opaque walls that is positionable over the disease site to exclude external light from the chamber, the chamber containing therein the at least one light emitting diode.

9. An optical probe as claimed in claim 8 in which the elongate member comprises:

a generally cylindrical member housing the optical fiber bundles that extend to a distal end of the cylindrical member; and a sleeve member that telescopes over the generally cylindrical housing, the overlap of the sleeve member with the distal end of the cylindrical member defining the chamber wherein slidable movement of the sleeve member with respect to the cylindrical member adjusts the length of the chamber to vary the size of the illumination spot at the disease site.

10. An optical probe as claimed in claim 9 in which the sleeve member is formed with a window for viewing inside the chamber to ensure proper positioning of the chamber over the disease site and a slidable cover to seal the window when the apparatus is in use.

11. An optical probe as claimed in claim 1 in which the free end of the sleeve member is cut at substantially 45 degrees to the longitudinal axis of the sleeve to avoid specular reflection.

12. A method for diagnosis of a disease selected from the group consisting of actinic keratosis, seborrheic keratosis, basal cell carcinoma, compound nevus and spider angioma at a skin disease site using spectral analysis comprising the steps of:

illuminating the disease site with a light source to generate fluorescence and reflectance light at the disease site;

collecting the generated fluorescence light;

conducting a spectral analysis of the collected light using a spectrometer;

determining spectral measurements of the fluorescence light and therefrom determining a 3-D spectrum of the fluorescence light; and examining the spectral measurements to make a diagnosis of the disease site.

13. A method as claimed in claim 12 including filtering the collected fluorescence light to filter out the excitation light.

14. A method as claimed in claim 12 in which a spectrometer card mounted in a personal computer is used to conduct a spectral analysis of the generated fluorescence and reflected light and display spectral measurements.

15. A method as claimed in claim 12 in which the step of collecting the generated fluorescence light involves collecting light from the disease site and the surrounding normal skin.

16. A method as claimed in claim 15 in which the step of examining the spectral measurements involves comparing the disease site spectrum to the spectrum of the surrounding normal skin.

17. A method as claimed in claim 16 including the step of generating a ratio spectrum by dividing the disease site spectrum by the spectrum of the adjacent normal skin.

18. A method as claimed in claim 12 in which the step of determining a 3-D spectrum of the fluorescence light further comprises generating a two-dimensional contour plot from the 3-D spectrum to generate a fluorescence excitation-emission matrix (EEM).

19. A method as claimed in claim 12 in which the step of determining a 3-D spectrum of the fluorescence light further comprises sectioning the 3-D spectrum at a fixed emission wavelength to generate a 2-D plot of fluorescence excitation spectrum.

20. A method as claimed in claim 12 in which the method further comprises generating a ratio matrix by dividing a 3-D spectrum from a lesion versus a 3-D spectrum from surrounding normal skin.

21. A method as claimed in claim 12 in which the method further comprises generating a subtractive matrix by subtracting a 3-D spectrum a lesion from a 3-D spectrum from surrounding normal skin.

* * * * *